United States Patent [19]

Mookherjee et al.

[11] Patent Number: 5,367,899

[45] Date of Patent: Nov. 29, 1994

[54] SYSTEM FOR PERFUME CREATION USING AROMA EMISSION ANALYSIS FROM A LIVING FRUIT AND FLOWER IN CLOSE PROXIMITY

[75] Inventors: Braja D. Mookherjee, Holmdel; Robert W. Trenkle, Brielle; Richard A. Wilson, Westfield, all of N.J.

[73] Assignee: International Flavors & Fragrances Inc., New York, N.Y.

[21] Appl. No.: 228,262

[22] Filed: Apr. 15, 1994

Related U.S. Application Data

[63] Continuation-in-part of Ser. No. 92,463, Jul. 16, 1993, which is a continuation-in-part of Ser. No. 988,337, Dec. 9, 1992, Pat. No. 5,269,169.

[51] Int. Cl.5 ............... G01N 30/86; G01N 33/48; A61K 7/46
[52] U.S. Cl. ............... 73/23.340; 73/23.42; 47/69; 512/5; 512/2; 512/3
[58] Field of Search ............... 73/23.34, 23.43; 47/69, 47/1.01

[56] References Cited

U.S. PATENT DOCUMENTS

| | | | |
|---|---|---|---|
| 2,837,912 | 6/1958 | Moncrieff | 73/23.34 |
| 5,263,359 | 11/1993 | Mookherjee et al. | 73/23.34 |
| 5,269,169 | 12/1993 | Trenkle et al. | 73/23.34 |

*Primary Examiner*—Thomas P. Noland
*Assistant Examiner*—J. David Wiggins
*Attorney, Agent, or Firm*—Arthur L. Liberman

[57] ABSTRACT

Described is a process for qualitatively and quantitatively substantially continuously analyzing the aroma emitted and rates of emission of the components thereof from a portion of the outer surface of a living fruit and from a living flower located within a specifically enclosed 3-dimensional space proximate said portion of the outer surface of said living fruit, simultaneously, using an aroma trapping device connected to the enclosed 3-dimensional space, and utilizing the resulting analysis for preparation of perfume compositions, perfumed articles and colognes. Also described is apparatus for carrying out such a process. The living fruit may, for example, be a living pineapple or a living nectarine growing on a nectarine tree. The living flower may, for example, be a living rose growing on a rose bush.

23 Claims, 8 Drawing Sheets

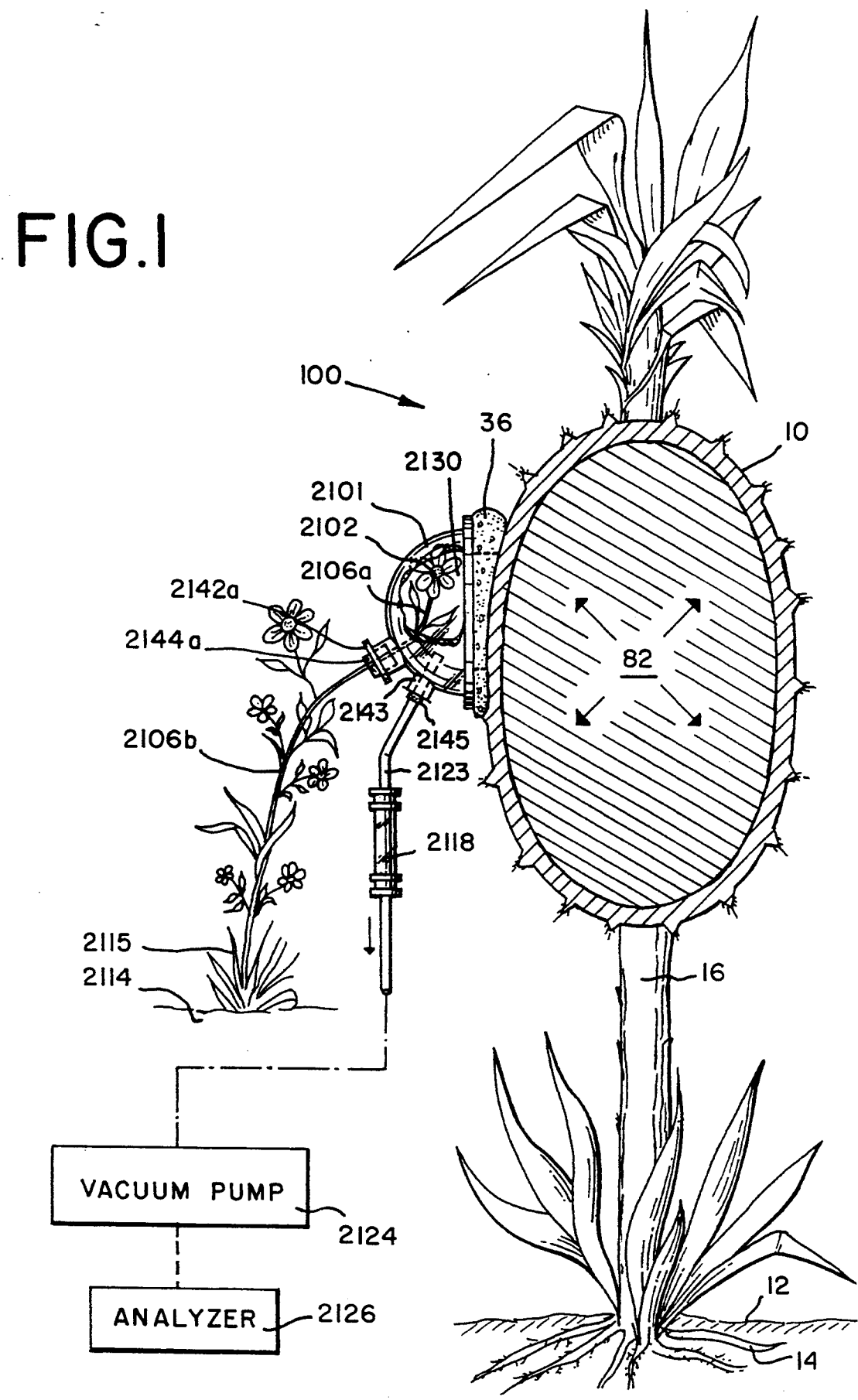

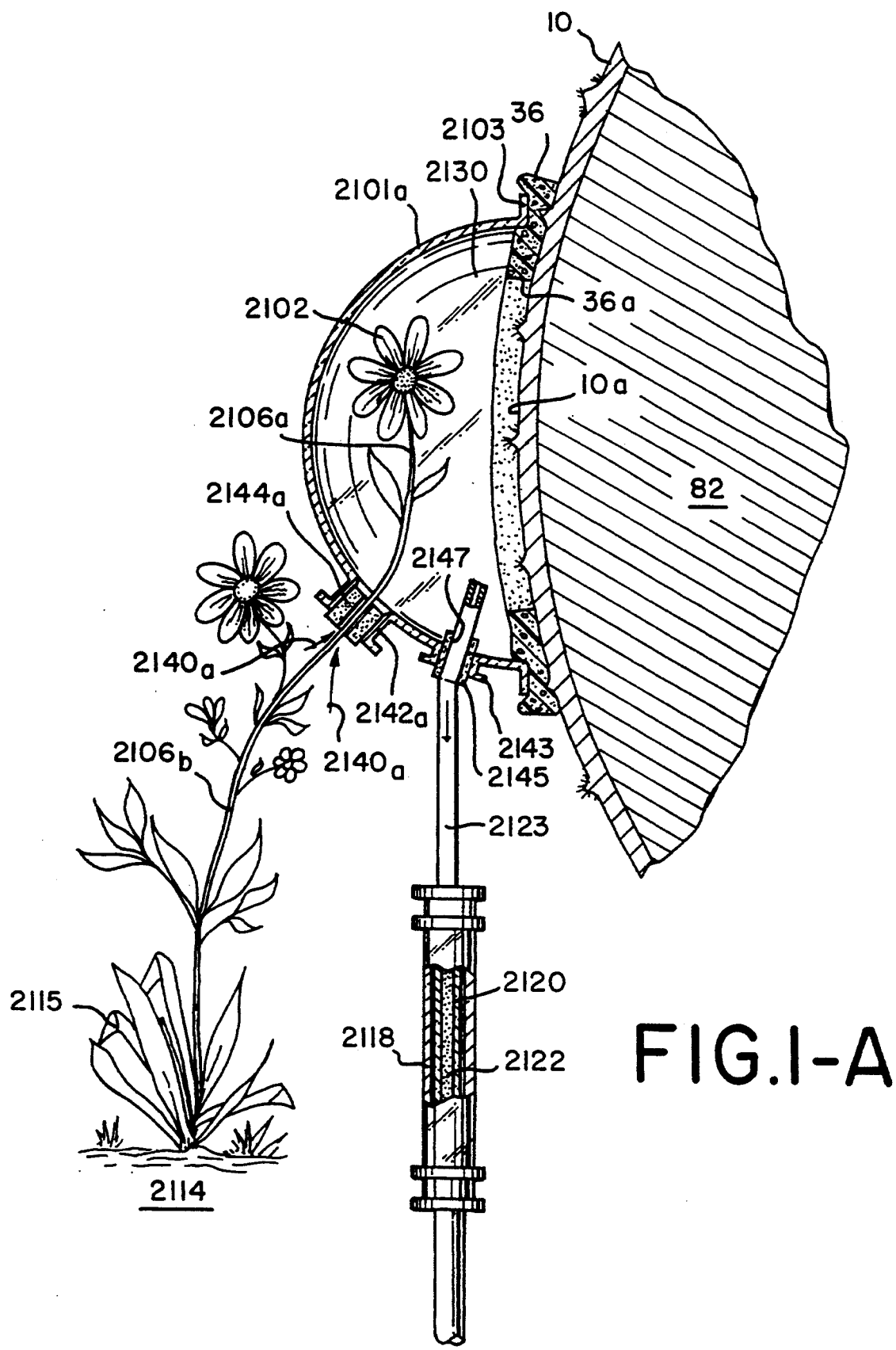
FIG.1-A

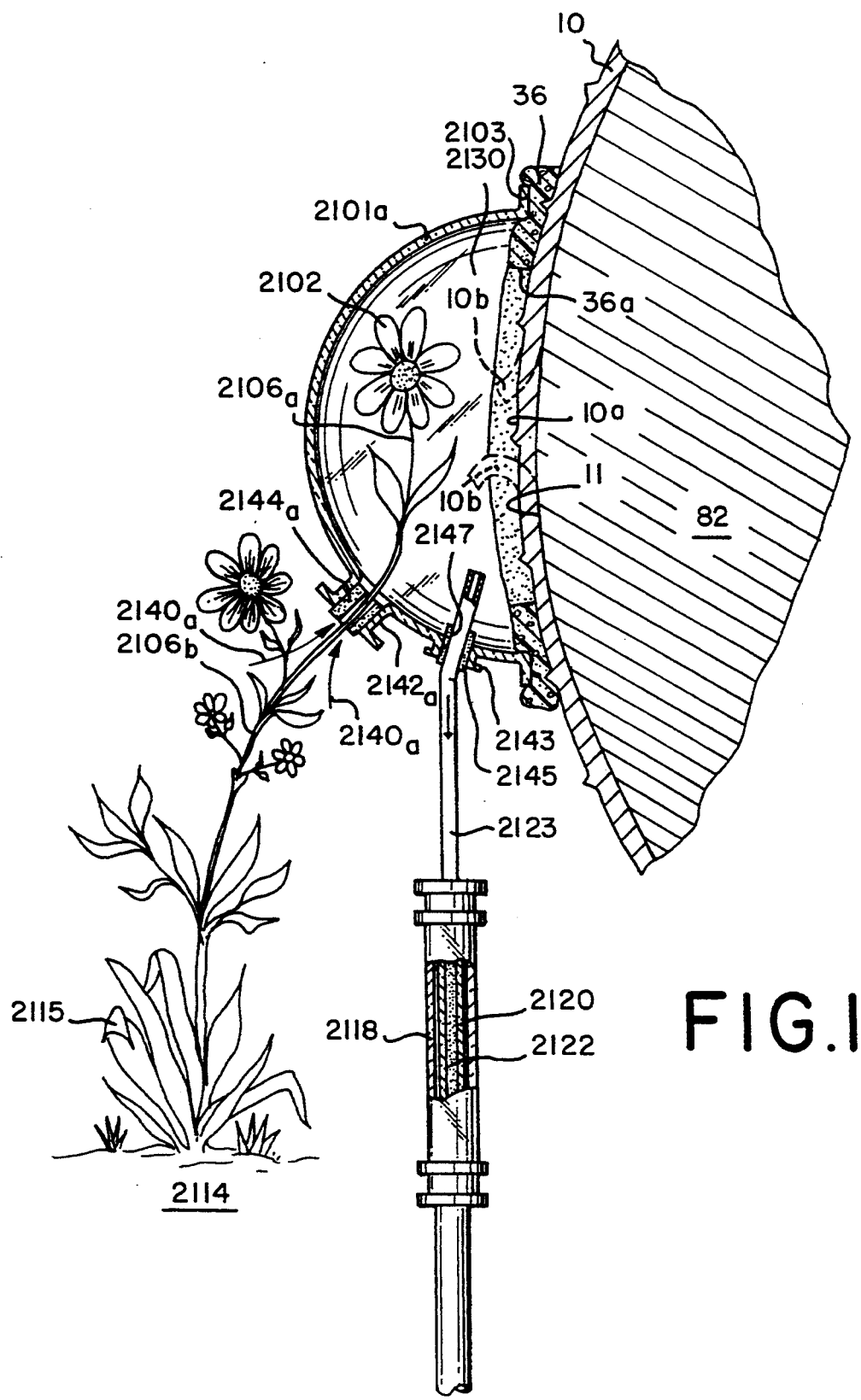
FIG. 1-B

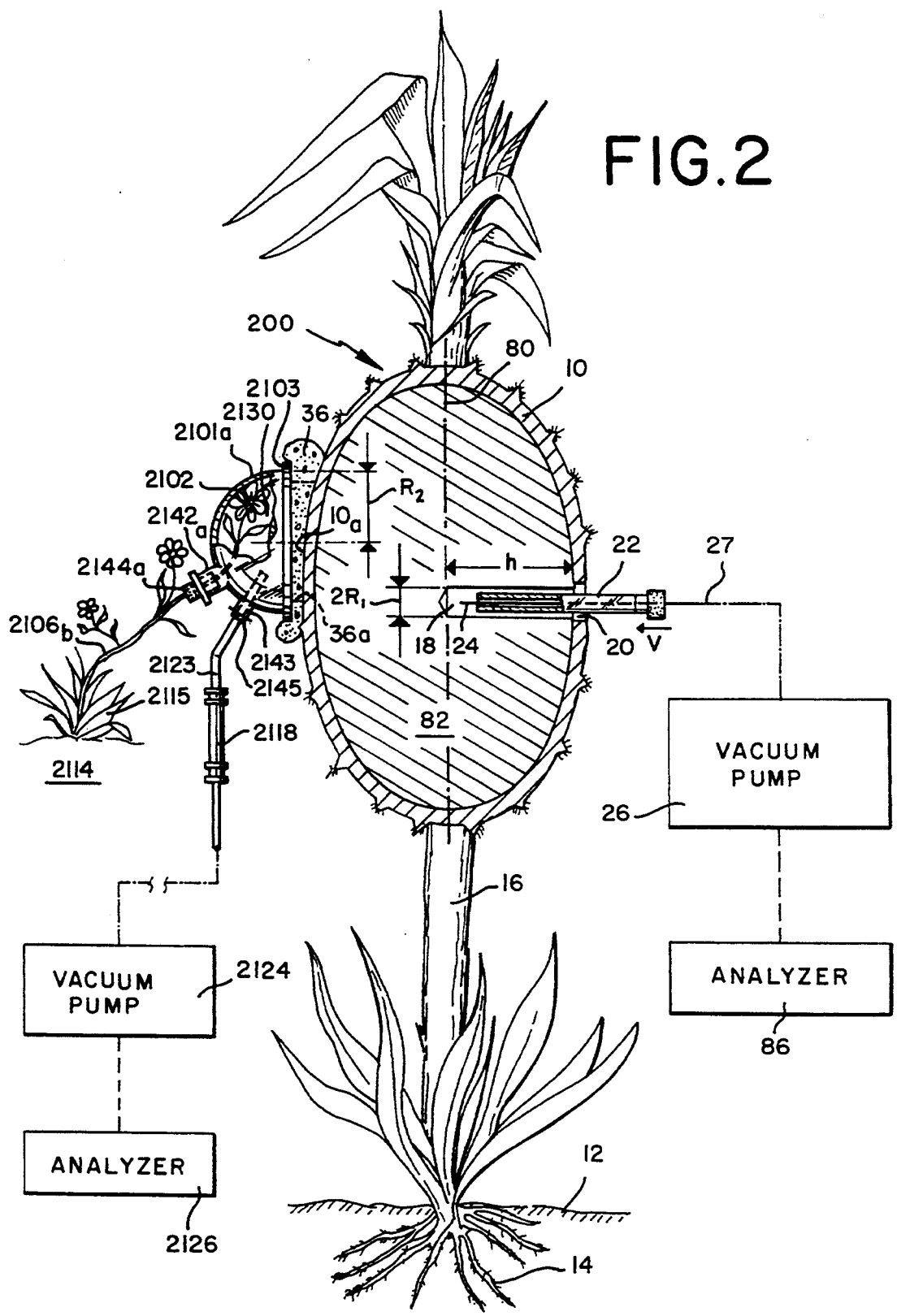

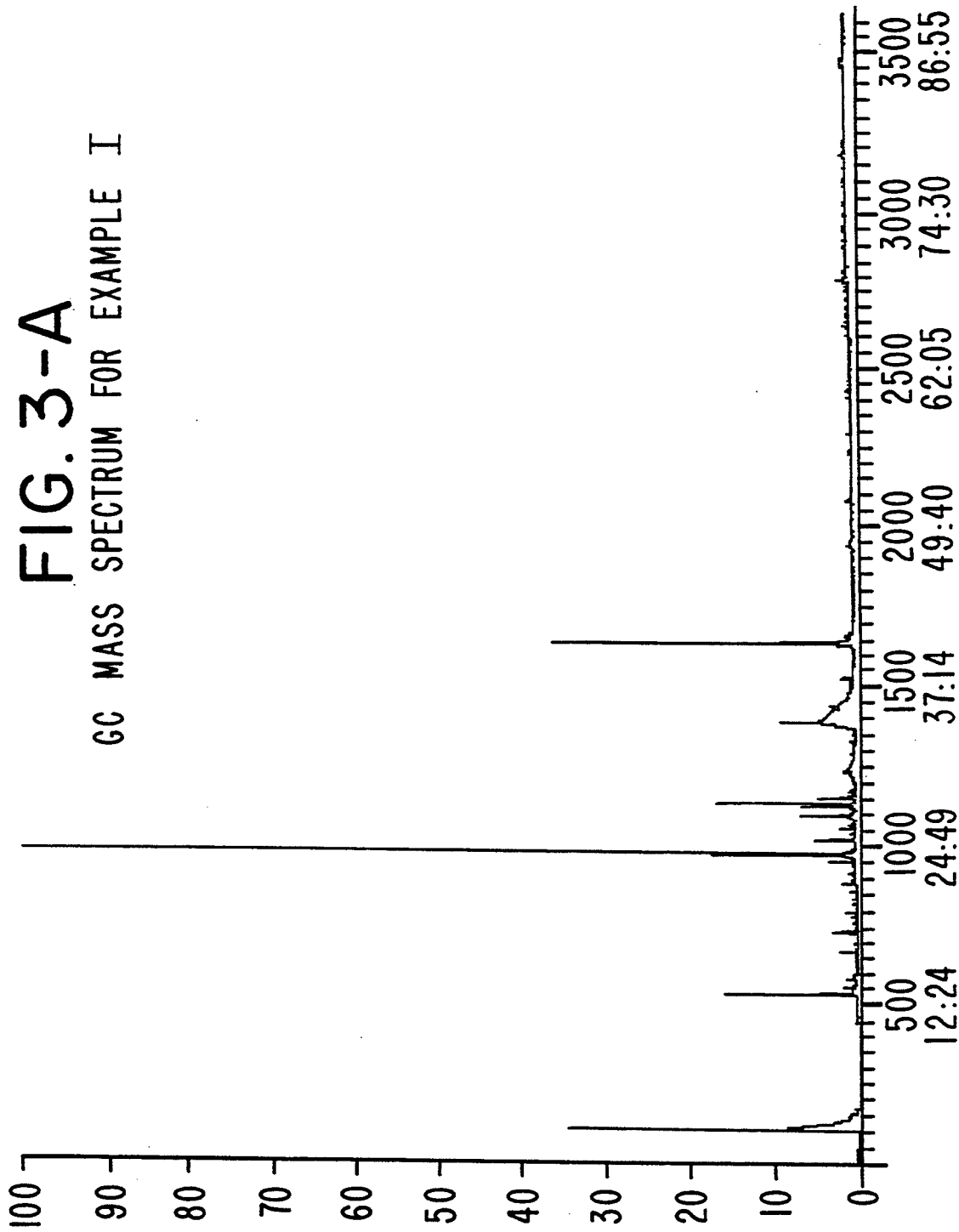
FIG. 3-A
GC MASS SPECTRUM FOR EXAMPLE I

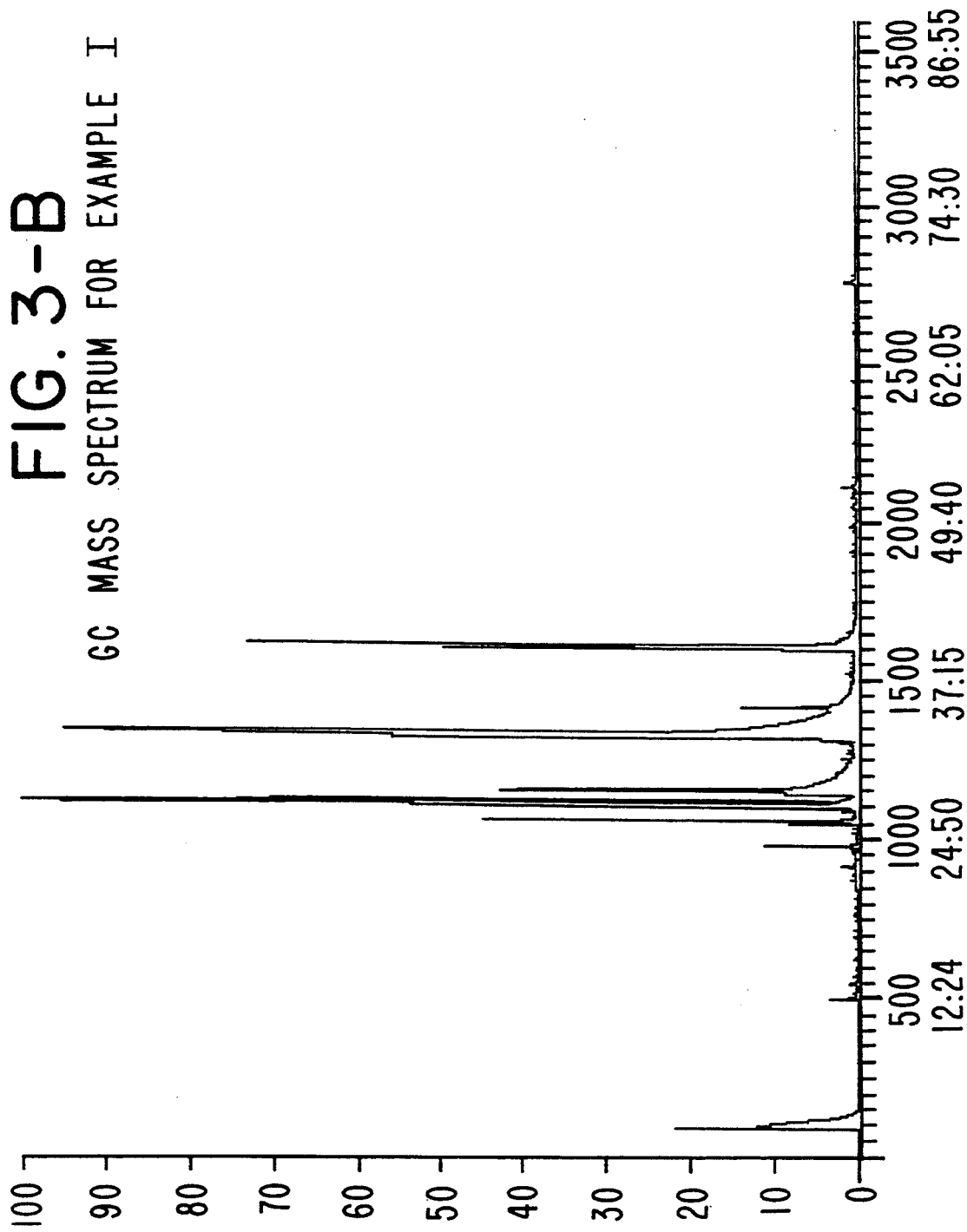

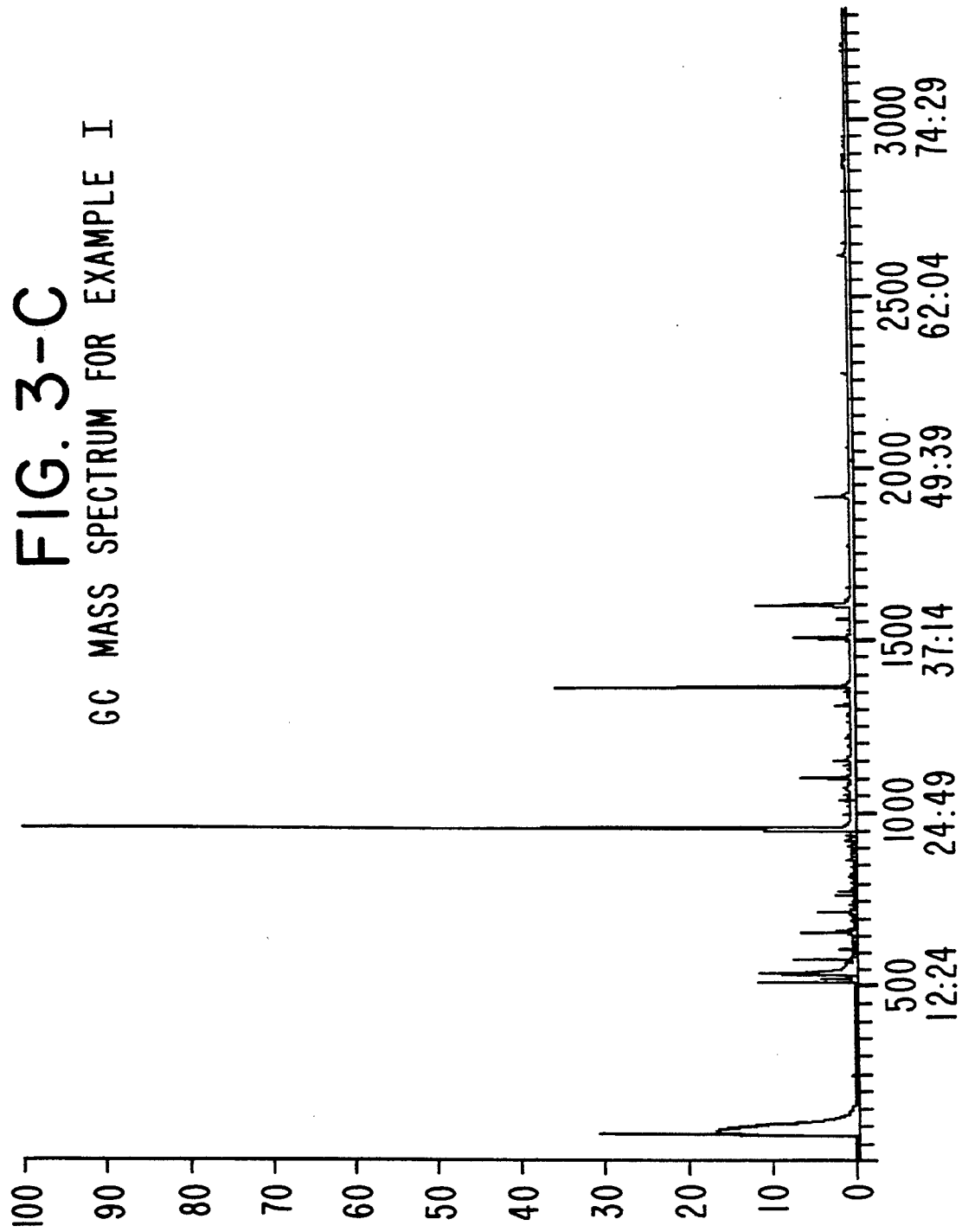
FIG. 3-C
GC MASS SPECTRUM FOR EXAMPLE I

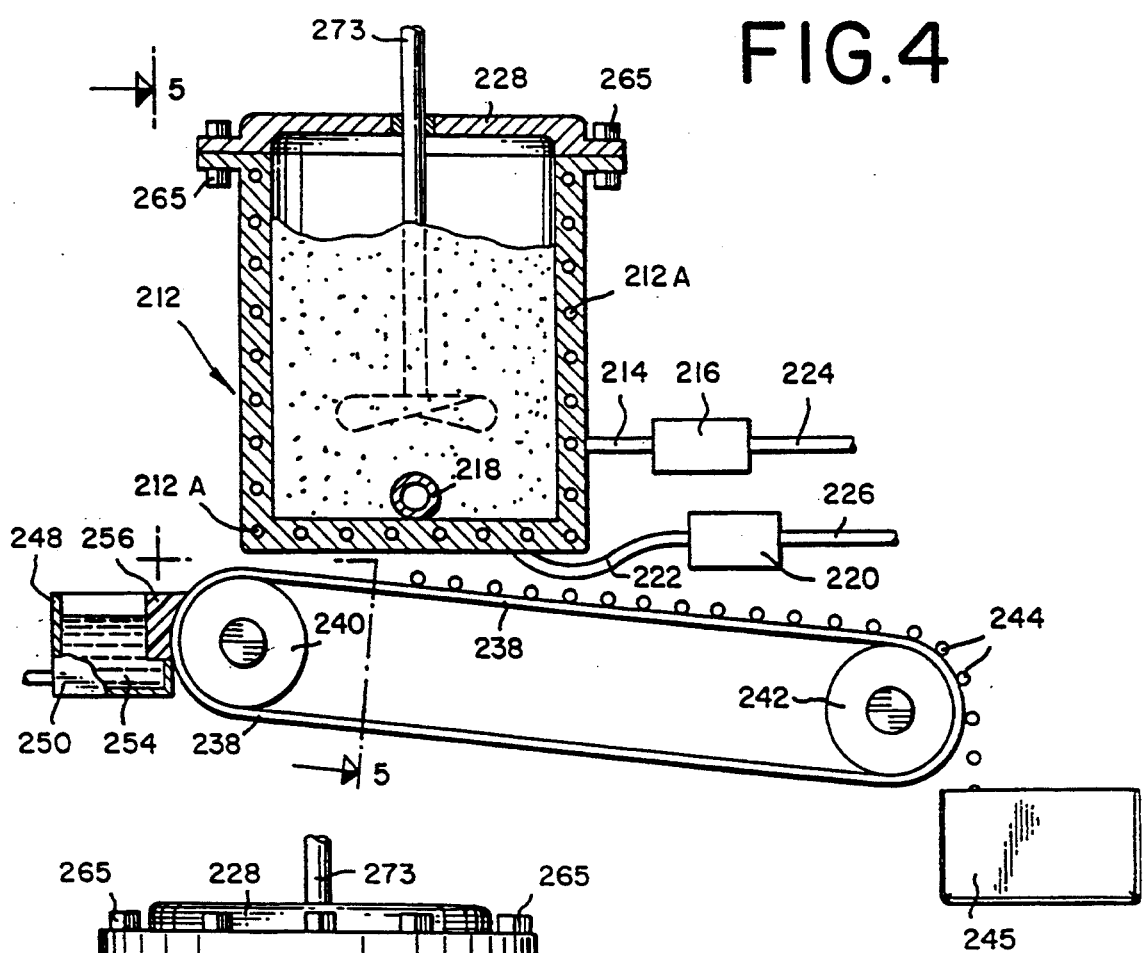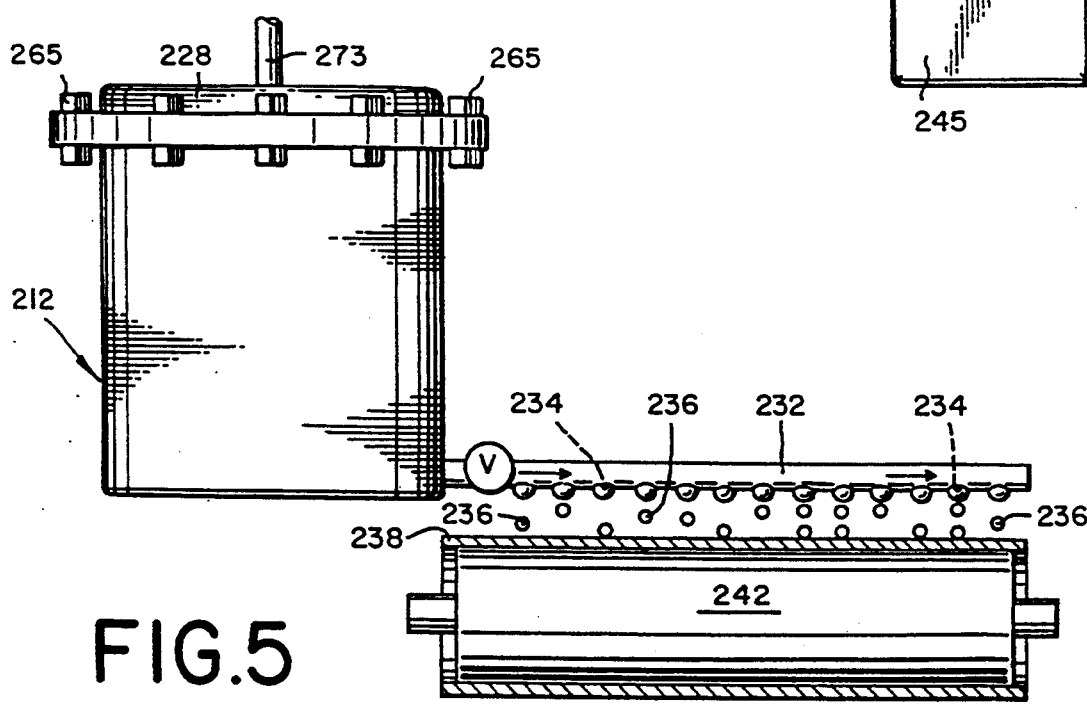

SYSTEM FOR PERFUME CREATION USING AROMA EMISSION ANALYSIS FROM A LIVING FRUIT AND FLOWER IN CLOSE PROXIMITY

This is a continuation-in-part (CIP) of U.S. Ser. No. 08/092,463 filed Jul. 16, 1993, which application for patent is still pending at this time, which is a continuation-in-part of U.S. Ser. No. 07/988,337 filed Dec. 9, 1992, which application is now U.S. Pat. No. 5,269,169 as issued on Dec. 14, 1993.

BACKGROUND OF THE INVENTION

Our invention concerns a process for qualitatively and quantitatively substantially continuously analyzing the aroma emitted and rates of emission of the aroma components thereof from a portion of the surface of a living fruit and from a living flower simultaneously at a given point in time over a given time period using a single enclosure to contain the living flower proximate and juxtaposed with the portion of the surface of the living fruit, and having aroma trapping means attached to the single enclosure; and apparatus for carrying out such a process. Our invention also concerns a process for preparing one or more perfume compositions comprising the steps of carrying out the aforementioned analysis or analyses and then, using the results of such analysis or analyses providing and admixing at least the major components found in the analysis, apparatus for carrying out such process, perfume compositions prepared using such apparatus and process, and perfumed articles and colognes containing such perfume compositions.

Uses of aromas evolved from living flowers and living fruits which are part of living plants or which are parts of living trees are highly sought after in the perfumery and flavor arts. Great difficulty has been experienced in attempting to capture and reproduce actual aroma ingredients of such living flowers or living fruits at various points in time relative to the maturation of the plant or tree on which the living flower or living fruit is growing.

In addition, a need has arisen for observation of the growth of living flowers and living fruits and a need for measuring such growth, standardizing the measurements of such growth at various times of plant or tree maturation and observing such growth; in an effort to optimize the marketing of perfume compositions based on living flower and living fruit components in conjunction with one another.

Mookherjee, et al, J.Ess.Oil Res., Volume 2, pages 85–90, (March/April 1989) [Title: "Live vs. Dead. Part II, A Comparative Analysis of the Headspace Volatiles of Some Important Fragrance and Flavor Raw Materials"] sets forth an examination of the headspace volatiles of living and picked tea rose, narcissus, osmanthus and spearmint comparatively using TENAX ® as the trapping adsorbent and GC/MS analysis ("Gas Chromatography/Mass Spectral Analysis") as the method of analysis. Mookherjee, et al discloses that it was found that the living rose possessed cis-3-hexenyl acetate (20.67%) as the major volatile component, whereas the major volatile component of the picked rose was 3,5-dimethoxy toluene. Mookherjee, et al further states that living narcissus flowers were found to contain benzyl acetate (44.0%), 3,4- and 3,5-dimethoxy toluene (35.0%) and indole (5.0%) whereas picked flowers contain benzyl acetate (30.43%), 3,4- and 3,5-dimethoxy toluene (18–39.5%) and indole (0.3–1.0%). Mookherjee, et al further states that osmanthus flowers (living) were found to possess beta-damascenone, dihydro-beta-ionol, and 4-keto-beta-ionone whereas these compounds were not detected in either air or nitrogen-purged picked flowers. Mookherjee further states that harvested spearmint possessed carvone (70.0%) and limonene (2.0%) in its headspace while the headspace of living spearmint was found to contain carvone (24.0%) and limonene (18.0%). Thus, Mookherjee, et al demonstrated that dramatic chemical changes take place in a plant or flower once it is harvested.

Trenkle, et al (U.S. Pat. No. 5,269,169 issued on Dec. 14, 1993) discloses a process for qualitatively and quantitatively substantially continuously analyzing the aroma emitted and rates of emission of the components thereof:

(i) from within; and
(ii) from the outer surface of a living fruit using simultaneously-operating aroma trapping devices connected to (a) the outer surface of the living fruit and (b) an internal portion of the living fruit.

Also described in Trenkle, et al, U.S. Pat. No. 5,269,169 is apparatus for carrying out such a process. The living fruit in Trenkle, et al, U.S. Pat. No. 5,269,169 may, for example, be a living pineapple or a living nectarine growing on a nectarine tree.

What is not disclosed in the prior art is the fact that when a portion of the surface of a living fruit and a living flower placed in an enclosed 3-space proximate and juxtaposed to the portion of the surface of the living fruit are exposed to a moving stream of air, the resulting aroma evolved simultaneously from both the portion of the surface of the living fruit and from the living flower is different in kind from the separate analyzed aromas of the separate living flower and the separate portion of the surface of the living fruit, and such difference gives rise to unexpected, unobvious and advantageous perfume compositions which have unobvious natural aroma qualities (that is, topnotes, middle notes and undertones).

U.S. Pat. No. 5,136,805 issued on Aug. 11, 1992 describes an air-tight flexible transparent container containing at least one living flower immersed in an aqueous suspension. Described in U.S. Pat. No. 5,136,805 is an article useful (i) for display purposes; and/or (ii) for analysis of the headspace in the container above the living flower when the container is fitted with a tube effecting communication of the internal 3-space (internal volume) of the container with outside analytical means and/or (iii) for aromatizing the environment surrounding the container when the container is fitted with a wick effecting communication of the internal 3-space (internal volume) of the container with the environment surrounding the container.

However, U.S. Pat. No. 5,136,805 does not teach or infer a technique for quantitatively and qualitatively substantially continuously analyzing the aroma emitted and rates of emission of the components thereof of a portion of the surface of a living fruit and of a living flower located in an enclosed 3-dimensional space proximate and juxtaposed with the portion of the surface of the living fruit, simultaneously, growing from plants or trees in a natural habitat where the plants or trees bearing such living flower and living fruit are outside of the enclosure containing the living flower.

THE INVENTION

Our invention covers a process for quantitatively and qualitatively substantially continuously analyzing the aroma emitted and rates of emission of the aroma components thereof from a portion of the surface of a living fruit and from a living flower (located in an enclosed 3-dimensional space proximate and juxtaposed to the portion of the surface of the living fruit) connected via a stem to a living tree or a living plant at a given point in time over a given period of time, using a single enclosure to contain the living flower attached to a small portion of its stem and having aroma trapping means attached to the enclosed 3-dimensional space; and apparatus for carrying out such process.

Our invention is also drawn to a process for quantitatively and qualitatively substantially continuously analyzing the aroma emitted and rates of emission of the components thereof:

(i) from within; and
(ii) from a portion of the outer surface of a living fruit and, simultaneously, from a living flower located in an enclosed 3-dimensional space proximate and juxtaposed with the portion of the surface of the living fruit.

Our invention is also intended to cover a process for preparing one or more perfume compositions comprising the steps of carrying out the aforementioned analysis or analyses and then using the results of such analysis or analyses, providing and admixing the major components found in the analysis or analyses, and apparatus for carrying out such process as well as perfume compositions prepared using such apparatus and process and perfumed articles and colognes containing such perfume compositions.

Examples of such living fruits useful in the practice of our invention are living pineapples and living nectarines. Examples of living nectarines are nectarines growing on a tree such as the red jewel nectarine tree (disclosed and claimed in U.S. Plant Pat. No. 8,013 issued on Oct. 27, 1992, the specification for which is incorporated herein by reference) and the red diamond nectarine tree (disclosed and claimed in U.S. Plant Pat. No. 3,165 the specification for which is incorporated herein by reference).

In addition, the process of our invention concerns, for example, such groups of species and/or varieties of living flowers as follows:

Group A
*Rosa Centifolia*
*Rosa gallica officinalis*
Flowers of the Rose Plant "Ausleap" as disclosed in U.S. Plant Patent 8153 issued on February 23, 1993, the specification for which is incorporated by reference herein.
Flowers from the Rose Plant- "Auscrim" as disclosed in U.S. Plant Patent 8154 issued on February 23, 1993, the specification of which is incorporated herein by reference.
Flowers from the Gazania plant called "Moorpark Yellow" as disclosed in U.S. Plant Patent 8161 issued on February 23, 1993 the specification for which is incorporated herein by reference.
Group B
*Crinum x powellii*
Flowers from the Carnation Plant named CFPC Day Dream as disclosed in U.S. Plant Patent 8232 issued on May 18, 1993 the disclosure of which is incorporated herein by reference.
Flowers from the Chrysanthemum Plant-Alhacultivar disclosed in U.S. Plant Patent 8227 issued on May 11, 1993 the specification for which is incorporated by reference herein.
Group C

*Mahonia japonica*
Flowers from the Rose Plant- "Ausram" as disclosed in U.S. Plant Patent 8156 issued on February 23, 1993 the disclosure for which is incorporated herein by reference.
Flowers from the Rose Plant- "Ausmit" as disclosed in U.S. Plant Patent 8157 issued on February 23, 1993 the specification for which is incorporated herein by reference.
Flowers from the Rose Plant- "Poulbero Variety" as disclosed in U.S. Plant Patent 8230 issued on May 18, 1993 the disclosure for which is incorporated herein by reference.
Group D
*Viola odorata* (sweet violet)
Flowers from the Rose Plant- "Jacsos" as disclosed in U.S. Plant Patent 8235 issued on May 25, 1993 the disclosure for which is incorporated by reference herein.
Flowers from the Chrysanthemum Plant-"Funrise Cultivar" as disclosed in U.S. Plant Patent 8241 issued on May 25, 1993 the disclosure for which is incorporated herein by reference.
Flowers from the Miniature Rose Plant-"Meinochot Variety" as disclosed in U.S. Plant Patent 8242 granted on June 1, 1993 the disclosure for which is incorporated herein by reference.
Flowers from the Chrysanthemum Plant named "Dark Eyes" as disclosed in U.S. Plant Patent 8244 issued on June 1, 1993 the disclosure for which is incorporated herein by reference.
Group E
White Jasminum Nitidum
Peach Colored Rose Fragrant Delight
Group F
Yellow Osmanthus Olive
Peach Rose Fragrant Delight
Group G
Ginger Lily Flower
Jasminum Odoratissimum Flower
Group H
Purple Heliotroprium Iowa
Jasminum Odoratissimum Flower
Group J
Dwarf Navel Orange Flower
Jasmin Nitidum Flower
Group K
Red Rose All That Jazz
White Ginger Lily Flower.

Examples of the "enclosed 3-dimensional space" are:
(i) a hemisphere, the planar opening of which is sealably enclosed by the living fruit surface portion;
(ii) a bifurcated hemisphere, the planar opening of which is sealably enclosed by the living fruit surface portion;
(iii) a right circular cylinder, with one open base enclosed by the living fruit surface portion;
(iv) a right circular cone, with its base open and sealably enclosed by the living fruit surface portion;
(v) a paraboloid, with its base open and sealably enclosed by the living fruit surface portion;
(vi) a frustum of a right circular cone with its major base open and sealably enclosed by the living fruit surface portion; and
(vii) a tetrahedron with its base open and sealably enclosed by the living fruit surface portion.

The process of our invention covers the steps of:
(a) providing a living fruit having a living fruit outer skin surface and a living fruit inner surface; said outer surface having a surface area S having a living fruit outer surface portion having a surface area $$KS$$

wherein $$0.25 \leq K \leq 0.03$$

(b) providing first analytical apparatus means comprising a first trapping tube means attached to first negative pressure pump means associated with chemical analysis means-(e.g., infrared analysis means; nuclear magnetic resonance analysis means; mass spectral analysis means and gas chromotographic analysis means);

(c) providing a living flower located within an enclosed 3-dimensional space proximate and juxtaposed to said living fruit outer surface portion, said living flower being connected to a living flower stem which, in turn, is connected to a living flower plant or living flower tree (for example, a rose bush);

(d) providing hollow flexible enclosure means surrounding said living flower having an inner enclosure means void and an outer enclosure means shell having an outer enclosure means surface and an inner enclosure means surface, said outer enclosure means shell encompassing said void and terminating at an enclosure rim means, said void (i) containing said living flower and (ii) being defined by said outer enclosure means shell and said enclosure rim means, said outer enclosure means shell having first and second insertion orifices, each extending from said outer enclosure means surface to said inner enclosure means void, said enclosure means being capable of sealably gripping said first outer surface portion of said living fruit;

(e) causing said enclosure means to (i) sealably grip said first outer surface portion of said living fruit at said enclosure rim means and (ii) surround said living flower whereby said living flower stem is fixedly held in place using said first insertion orifice;

(f) inserting said first trapping tube means through said second insertion orifice causing it to be extended into said enclosure means void;

(g) engaging said first negative pressure pump means whereby components of (i) the aroma evolving from said outer surface portion of said living fruit and (ii) the aroma evolving from said living flower, are simultaneously entrapped in said first trapping tube means; and (h) analyzing the contents of said first trapping Lube means using said first chemical analysis means substantially continuously and simultaneously.

Preferably, the enclosure means is a transparent hemisphere, the planar opening of which is sealably enclosed by the living fruit surface portion. Such hemisphere is preferably a bifurcated hemisphere with the two quarter spheres being clamped together in a sealable fashion. If the radius of such hemisphere is $R_2$ then its volume is:

$$[\tfrac{2}{3}\pi R_2^3]$$

and the surface area of the portion of the living fruit surface is approximately:

$$[\pi R_2^2].$$

A living flower within the enclosure may have a mathematically constructed volume around the flower assuming that the volume is a sphere having a radius $R_3$ the length of the longest petal of the flower and its volume would be:

$$\tfrac{4}{3}\pi R_3^3.$$

Obviously then:

$$\tfrac{4}{3}\pi R_3^3 < \tfrac{2}{3}\pi R_2^3$$

and it follows that:

$$4R_3^3 < 2R_2^3$$

and $$2R_3^3 < R_2^3$$

and it then follows that $$\sqrt[3]{2}\, R_3 < R_2$$

and $$R_3 < \left[ \frac{1}{\sqrt[3]{2}} (R_2) \right].$$

Preferably, however, the volume of the mathematically constructed sphere about the living flower is one-half of the volume of the enclosure. Thus, preferably:

$$R_3 = \left[ \frac{1}{\sqrt[3]{4}} (R_2) \right].$$

Our invention also covers a process for qualitatively and quantitatively substantially continuously analyzing the aroma emitted and rates of emission of the components thereof:

(i) from within; and
(ii) from the outer surface of a living fruit simultaneously with a living flower located in a 3-dimensional enclosure proximate to and juxtaposed to a portion of the outer surface of the living fruit, consisting essentially of the steps of:

(a) providing a living fruit located on a given central axis having a living fruit outer skin surface and a living fruit inner surface; said outer surface having a surface area S and having a living fruit outer surface portion having a surface area:

$$KS$$

wherein $$0.25 \leq K \leq 0.03$$

said surface portion being located at a given distance from the central axis and an inner volume surrounding said central axis and encompassed by said living fruit outer skin surface;

(b) removing a depth core section from said inner volume running from said outer skin surface to a depth of from about half-way up to entirely to the central axis, into said inner volume along a directional vector "V" extending substantially radially from said central axis to said outer skin surface within said inner volume;

(c)-1 providing first analytical apparatus means comprising a first trapping tube means attached to first negative pressure pump means associated with chemical analysis means (e.g., GC-mass spectral, nuclear magnetic resonance spectral, raman spectral and infrared spectral analytical equipment);

(c)-2 providing second analytical apparatus means comprising a second trapping tube means attached to second negative pressure pump means associated with second chemical analysis means;

(d) providing a living flower located within an enclosed 3-dimensional space proximate and juxtaposed to said living fruit outer surface portion, said living flower being connected to a living flower stem, which, in turn, is connected to a living flower plant or living flower tree (e.g., a pineapple plant);

(e) providing hollow flexible enclosure means surrounding said living flower (e.g., a spherical cup-like enclosure) having an inner enclosure means void and an outer enclosure means shell having an outer enclosure means surface and an inner enclosure means surface, said outer enclosure means shell encompassing said void and terminating at an enclosure rim means, said void (i) containing said living flower and (ii) being defined by said outer enclosure means shell and said enclosure rim means, said outer enclosure means shell having first and second insertion orifices each extending from said outer enclosure means surface to said inner enclosure means void, said enclosure means being capable of sealably gripping said first outer surface portion of said living fruit;

(f) causing said enclosure means to (i) sealably grip said first outer surface portion of said living fruit at said enclosure rim means and (ii) surround said living flower whereby said living flower stem is fixedly held in place using said first insertion orifice;

(g) inserting said second trapping tube means into said core section void along said directional vector "V";

(h) inserting said first trapping tube means through said second insertion orifice causing it be extended into said enclosure means void;

(j) simultaneously engaging said first negative pressure pump means and said second negative pressure pump means whereby components of the aroma evolving from said outer surface portion of said living fruit and evolving from said living flower are entrapped in said first trapping tube means and components of the aroma evolving from within said living fruit are entrapped in said second trapping tube means simultaneously; and (k) analyzing the contents of said first trapping tube means using said first chemical analysis means and said second trapping tube means using said second chemical analysis means substantially continuously and substantially simultaneously.

Of course when the living fruit is one that has a pit such as a peach or a nectarine or a plum, then obviously the depth core can only extend to the outer surface of the pit, and preferably the depth core should extend about one-third of the way into the fruit without touching the surface of the pit. Thus, for example, in the case of a pineapple the depth core would be about ¼" in diameter and the tube entering the core containing the trapping material would be approximately 3/16" in diameter and about 6" in length. In the tube would be a trap such as a TENAX® trap which would be ⅛" in diameter and 4" in length, for example.

Thus, various trapping materials are useful in the practice of our invention in the trap used in trapping the aroma components emitted from within the totally enclosed 3-dimensional space by the living flower and by the surface (broken or unbroken) portion of the living fruit. TENAX® is a preferable material. Various forms of TENAX® are useful, for example, TENAX®-GC. TENAX® is a registered trademark of ENKA N. V. of The Kingdom of The Netherlands (CAS Registration No. 24938-68-9). Various forms of TENAX® and methods of producing same are described in the following U.S. Letters Patent, the disclosures of which are incorporated herein by reference:

U.S. Pat. No. 3,400,100 issued on Sep. 3, 1968 ("Process For The Preparation Of Polyphenylene Ethers")

U.S. Pat. No. 3,644,227 issued on Feb. 22, 1972 ("Separation Of Poly(2,6-Dimethyl-1,4-Phenyleneoxide) from its blends with other polymers")

U.S. Pat. No. 3,703,564 issued on Nov. 21, 1972 ("Bis[Polyphenyleneoxide]-Ester Block Copolymers")

U.S. Pat. No. 4,431,779 issued on Feb. 14, 1984 ("Polyetheramide-Polyphenylene Ether Blends")

U.S. Pat. No. 4,801,645 issued on Jan. 31, 1989 ("Thermoplastic Resin Composition")

TENAX®-GC is actually a polyphenyleneoxide defined according to the structure:

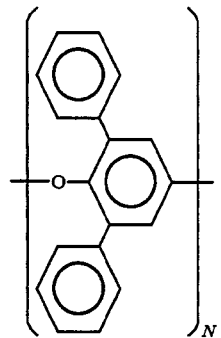

wherein N is an integer of from about 100 up to about 150.

Other trapping materials useful in the practice of our invention are as follows: Activated Carbon marketed by Aldrich Chemical Company of 1001 West Saint Paul Avenue, Milwaukee, Wis. 53233 (Catalog Nos. 16, 155-1; 29, 259-1; 24, 223-3; 24, 224-1 and 24, 227-6); Activated Alumina marketed by Sigma Chemical Company of St. Louis, Mo. (Catalog Nos. A8753; A8878; A9003; A1772; A1522 and A2272); Silica Gels marketed by Sigma Chemical Company, for example, Catalog Nos. S4004; S6628 and H8506; CHROMOSORB® (registered trademark of the Johns-Manville Company of Manville, N.J.) such as CHROMOSORB® LC-1; CHROMOSORB® LC-2; CHROMOSORB® LC-3, and CHROMOSORB® LC-7 marketed by the Sigma Chemical Company under Catalog Nos. C 0641, C 0766, C 5517 and C 6269.

The process of our invention may be further modified wherein radiation from one or more radiation sources such as an infrared radiation source and/or an ultraviolet radiation source connected to an electric power supply is emitted in a direction from one or more radiation sources and is directed into the enclosed 3-dimensional space containing the living flower and proximate to and juxtaposed to the portion of the surface of the living fruit. The radiation source(s) can be a plurality of sources directed to the living flower or a single radiation source or a multitude of radiation sources. The use of such infrared or ultraviolet radiation will give rise to an alteration in the aroma composition and hence the aroma components trap, evolved by the living flower and evolved from the broken or unbroken surface portion of the living fruit within the single totally enclosed 3-dimensional space.

Furthermore, a plurality of perfume compositions containing at least the major components of the aroma emitted by the living flower and the surface portion of the living fruit may be produced by carrying out a process comprising the steps of:

(i) carrying out the aforementioned process;

(ii) separately providing from independent sources at least the major aroma components found by the analysis of each of the steps of the above processes; and (iii) separately admixing each of the groups of components to form separate perfume compositions.

By the same token, the apparatus of our invention for qualitatively and quantitatively substantially continuously analyzing the emitted aroma and rates of emission of the aroma components thereof from a portion of the broken or unbroken skin surface of a living fruit and of a living flower located in an enclosed 3-dimensional space proximate and juxtaposed to the broken or unbroken skin surface of the living fruit comprises:

(a) a living fruit having a living fruit outer skin surface and a living fruit inner surface, said outer surface having a surface area S and having a living fruit outer surface portion having a surface area:

$$KS$$

wherein $$0.25 \leq K \leq 0.03:$$

(b) first analytical apparatus means comprising first trapping tube means attached to first negative pressure pump means associated with first chemical analysis means (for example, infrared spectral analysis means; nuclear magnetic resonance spectral analysis means; GC/mass spectral analysis means or Raman spectral analysis means);

(c) a living flower (such as a rose or a carnation) located within an enclosed 3-dimensional space (e.g., a bifurcated transparent hemisphere fabricated from glass or a clear acrylic polymer) proximate and juxtaposed to said living fruit outer surface portion (broken or unbroken) said living flower being connected to a living flower stem, which, in turn, is connected to a living flower plant or a living flower tree (e.g., a rose bush);

(d) hollow flexible or rigid enclosure means surrounding said living flower having an inner enclosure means void and an outer enclosure means shell (e.g., a clear glass bifurcated hemisphere), said outer enclosure means shell encompassing said void and terminating at an enclosure rim means, said void (i) containing said living flower and (ii) being defined by said outer enclosure means shell and said enclosure rim means, said outer enclosure means shell having first and second insertion orifices each of which extends from said outer enclosure means surface to said inner enclosure means void, said enclosure means (i) sealably gripping said first outer surface portion of said living fruit (for example, using an adhesive sealer such as a bisphenol-a-epichlorohydrin epoxy resin having a molecular weight of approximately one thousand) and (ii) surrounding said living flower whereby said living flower stem is fixedly held in place using said first insertion orifice, said first trapping tube means being inserted through said second insertion orifice causing it to be extended into said enclosure means void;

whereby when said first negative pressure pump means is engaged, components of the aroma evolving (i) from said outer surface portion of said living fruit and (ii) said living flower are entrapped in said first trapping tube means, simultaneously, enabling the contents of said first trapping tube means to be continuously analyzed substantially simultaneously using said first chemical analysis means.

Optionally, the apparatus of our invention may comprise:

(a) a living fruit located on a given central axis having a living fruit outer skin surface and a living fruit inner surface, said outer surface (which may be broken or unbroken; or which may be peeled away to expose an inner surface) having a surface area S and having a living fruit outer surface portion (or inner surface portion) having a surface area:

$$KS$$

wherein $$0.25 \leq K \leq 0.03$$

said living fruit outer skin surface portion or said living fruit inner surface portion being located at a given distance, "h" from said central axis; an inner volume surrounding said central axis and encompassed by said living fruit outer skin surface; a depth core section removed from said inner volume running from said outer skin surface (at a location substantially apart from the location of the living fruit outer surface portion) to a depth of from about $$"\tfrac{1}{2}h"$$

up to "h" into said inner volume along a directional vector "V" extending substantially radially from said central axis to said outer skin surface within said inner volume, said depth core section having an effective diameter "$D_1$ equal to $2 \times$(effective radius, $R_1$) and a core section volume ranging from about $$\pi R_1^2 h$$

down to about $$\frac{\pi R_1^2 h}{2}$$

thereby forming a core section void within said living fruit;

(b)-1 first analytical apparatus means comprising first trapping tube means attached to first negative pressure pump means associated with first chemical analysis means (e.g., infrared analysis means; nuclear magnetic resonance analysis means; GC-mass spectral analysis means and Raman spectral analysis means);

(b)-2 second apparatus means comprising second trapping tube means attached to second negative pressure pump means associated with second chemical analysis means;

(c) a living flower located within an enclosed 3-dimensional space proximate and juxtaposed to the living fruit outer surface portion, with the living flower being connected to a living flower stem, which, in turn, is connected to a living flower plant or a living flower tree (such as a rose bush);

(d) hollow flexible enclosure means or hollow rigid enclosure means which may or may not be transparent, surrounding the living flower, having an inner enclosure means void and an outer enclosure means shell having an outer enclosure means surface and an inner enclosure means surface, said outer enclosure means shell encompassing said void and terminating at an enclosure rim means (with the hollow flexible enclosure or hollow rigid enclosure being, for example, glass or a transparent polymer such as a transparent acrylic resin), said void (i) containing said living flower and (ii) being defined by said outer enclosure means shell and said enclosure rim means, said outer enclosure means shell having first and second insertion orifices each extending from said outer enclosure means surface to said inner enclosure means void, said enclosure means being capable of sealably gripping said first outer portion of said living fruit (for example, an adhesive type resin such as an epoxy resin which is a linear polymer of epichlorohydrin and bisphenol-A) with the flexible or rigid enclosure means preferably being a hemispherically shaped cup means with the inner volume of the cup means being about:

$$[\tfrac{2}{3}\pi R_2^3]$$

(e) said first trapping tube means being inserted through said first insertion orifice causing it to be extended into said enclosure means void;

(f) said second trapping tube means being inserted into said core section void along said directional vector "V";

whereby when the said first negative pressure pump means and said second negative pressure pump means are simultaneously engaged, components of the aroma evolving from (i) said living flower and said outer surface portion (broken or unbroken) of said living fruit are entrapped in said first trapping tube means and (ii) components of the aroma evolving from within said living fruit are entrapped in said second trapping tube means, simultaneously, enabling the contents of said first trapping tube means and said second trapping tube means to be continuously analyzed substantially simultaneously using said first and second chemical analysis means.

The analysis means may be GC-MS apparatus (gas chromatography/mass spectral analysis apparatus) taken alone or taken further together with infrared analysis equipment and nuclear magnetic resonance analysis equipment. In addition, Raman spectral analysis equipment may also be used in the analysis means for analyzing the aroma components evolved by the living flower and the surface of the living fruit and optionally, the inner part of the inner portion of the living fruit.

The negative pressure pump means of our invention useful in the practice of our invention is preferably a vacuum pump of the "Low Flow" variety, for example, "Low Flow" pumps marketed by the Ametek Company of Largo, Fla. 34643 (the Ametek Constant Flow Sampler).

The aroma evolved from (i) the living flower in the enclosed 3-dimensional space proximate and juxtaposed to the surface portion of the living fruit; (ii) the surface portion (broken or unbroken) of the living fruit proximate and juxtaposed to the 3-dimensional space in which the living flower is located; and, optionally, (iii) the inner core of the living fruit, is hereinafter indicated to be a "living flower/living fruit aroma". The perfume composition created as a result of combining at least the major components of such aroma, obtaining them from natural or synthetic sources, is hereinafter indicated to be a "living flower/living fruit fragrance composition".

Thus, at least one of the living flower/living fruit fragrance compositions produced according to the process of our invention and one or more auxiliary perfume ingredients including, for example, alcohols, aldehydes, nitriles, esters, cyclic esters, ketones, ethers, synthetic essential oils and natural essential oils may be admixed so that the combined odors of the individual components produce a pleasant and desired fragrance particularly and preferably in the fruity/floral fragrance area.

Such perfume compositions usually contain (a) the main note or "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh smelling materials.

In perfume compositions, it is the individual components which contribute to its particular olfactory characteristics, but the overall effect of the perfume composition will be the sum of the effects of each of the ingredients. Thus, one or more of the living flower/living fruit fragrance compositions of our invention and one or more auxiliary perfume ingredients can be used to alter the aroma characteristics of a perfume composition, for example, by utilizing or moderating the olfactory reaction contributed by at least one other ingredient in the composition.

The amount of at least one of the living flower/living fruit fragrance compositions of our invention useful in perfume compositions for augmenting or enhancing floral, fruity, magnolia and jasmine aromas may vary from about 1% by weight of the perfume composition up to 100% by weight of the perfume composition (the entire composition can be composed of the living flower/living fruit fragrance components determined by the practice of our invention).

At least one of the living flower/living fruit compositions of our invention and, if desired, one or more auxiliary perfume ingredients can be used to impart floral, fruity aroma nuances, topnotes and undertones to soaps, anionic, cationic, nonionic or zwitterionic detergents, fabric softener compositions, fabric softener articles, cosmetic powders, hair preparations and the like. The amount employed can range up to 100% by weight of the fragrance components and can range up to approximately 0.5% of the weight of the perfumed article and will depend upon considerations of cost, nature of the end product, the effect desired on the finished product and the particular fragrance sought.

At least one of the living flower/living fruit fragrance compositions of our invention and, if desired, one or more auxiliary perfume ingredients are useful, taken alone or in perfume compositions as olfactory components in anionic, cationic, nonionic or zwitterionic detergents, soaps, fabric softener compositions, fabric softener articles for use in clothes dryers (e.g., "BOUNCE ®", a registered trademark of the Procter & Gamble Company of Cincinnati, Ohio), space odorants and deodorants, perfumes, colognes, toilet waters, bath preparations, such as lacquers, brilliantines, creams, deodorants, hand lotions and sun screens; powders such as talcs, dusting powders, face powders and the like.

When used as an olfactory component in perfume compositions or perfumed articles, such as anionic, cationic, nonionic, or zwitterionic detergents and fabric softener compositions and fabric softener articles (e.g., for use in clothing dryers) as little as 0.05% of at least one of the living flower/living fruit fragrance compositions of our invention and, if desired, one or more auxiliary perfume ingredients will suffice to impart various fruity, floral aroma nuances. Generally, no more than 0.5% of at least one of the living flower/living fruit perfume compositions of our invention and, if desired, one or more auxiliary perfume ingredients based on the ultimate end product is required in the perfumed article. It should be noted however, that in "perfumed polymers" (as further specified in the DETAILED DESCRIPTION OF THE DRAWINGS section of our invention set forth, infra), the amount of the living flower/living fruit perfume composition of our invention and, if desired, one or more auxiliary perfume ingredients may be as much as 45%, based on the amount of perfumed polymer. Such perfumed polymers are microporous polymers containing in the interstices thereof the living flower/living fruit perfume composition of our invention and, if desired, one or more auxiliary perfume ingredients.

In addition, the living flower/living fruit perfume composition or fragrance composition of our invention can contain a vehicle or carrier for at least one of the living flower/living fruit perfume compositions of our invention and, if desired, one or more auxiliary perfume ingredients. The vehicle can be a liquid such as a non-toxic alcohol, a non-toxic glycol or the like (for example, propylene glycol). The carrier can also be an absorbent solid, such as a gum (e.g., gum arabic, xanthan gum or guar gum) or components for encapsulating the composition (such as gelatin as by means of coacervation).

It will thus be apparent that at least one of the living flower/living fruit compositions of our invention and, if desired, one or more auxiliary perfume ingredients can be used to alter the sensory properties, particularly organoleptic properties of a wide variety of consumable materials.

BRIEF DESCRIPTION OF THE DRAWINGS

FIG. 1 is a cut-away side elevation view of one embodiment of the apparatus of our invention showing a cut-away side elevation view of a living pineapple and a living flower located in a 3-dimensional space proximate to and juxtaposed to an unbroken surface of a living pineapple wherein the head space of the living pineapple and the headspace of the living flower are being quantitatively and qualitatively substantially continuously analyzed for aroma emitted and rate of emission of the components thereof:

(i) from an outer surface portion of the living pineapple; and (ii) from a living flower located in a 3-dimensional enclosed hemispherical space proximate and juxtaposed to the unbroken surface portion of living pineapple, simultaneously.

FIG. 1A is a detailed cross section view of that part of the drawing of FIG. 1 showing, in detail, the enclosed hemispherical 3-dimensional space containing a living flower proximate and juxtaposed to an unbroken surface surface portion of the living pineapple.

FIG. 1B is a detailed cross section view of a portion of the cut-away side elevation view of the living pineapple of FIG. 1 showing in detail the enclosed hemispherical 3-dimensional space containing the living flower proximate and juxtaposed to a broken surface portion of the living pineapple.

FIG. 2 is a schematic drawing showing a cut-away side elevation view of a living pineapple and a living flower located in an enclosed hemispherical 3-dimensional space proximate and juxtaposed to an unbroken surface portion of a living pineapple wherein the headspace of the living pineapple surface portion and the headspace of the living flower as well as the headspace of the internal part of the living pineapple are being quantitatively and qualitatively substantially continuously analyzed for the aroma emitted and rate of emission of aroma components thereof:

(i) from within; and (ii) from the outer surface portion of the living pineapple and;

(iii) from the living flower simultaneously.

FIG. 3A is a GC-mass spectrum of the aroma components of a composition evolved (i) from the unbroken surface portion of a living yellow pineapple and (ii) from a living orange rose (Cary Grant) located in an enclosed hemispherical 3-dimensional space proximate and juxtaposed to said living pineapple unbroken surface portion when using the apparatus FIG. 1 and 1A according to Example I.

FIG. 3B is a GC-mass spectrum for the aroma components evolved from orange rose (Cary Grant) alone when using the apparatus of FIGS. 1 and 1A according to Example I.

FIG. 3C is a GC-mass spectrum for the aroma components evolved from a surface portion (unbroken) of yellow pineapple, alone, when using the apparatus of FIGS. 1 and 1A according to Example I.

FIG. 4 represents a cut-away side elevation view of apparatus used in forming perfumed polymers containing at least one of the living flower/living fruit fragrance compositions of our invention.

FIG. 5 is a front view of the apparatus of FIG. 4 looking in the direction of the arrows.

DETAILED DESCRIPTION OF THE DRAWINGS

FIGS. 1, 1A and 1B set forth apparatus 100 for qualitatively and quantitatively substantially continuously analyzing the aroma evolved:

(i) from a portion 10a of the outer surface 10 of a living pineapple having inner portion 82, stem 16, roots 14 and growing in the ground 12; and (ii) from a living flower 2102 located within a 3-dimensional space 2130 proximate and juxtaposed to said portion of the outer surface 10a of the living pineapple consisting essentially of:

(a) a living pineapple having a living pineapple outer skin surface 10 and a living pineapple inner surface 11, said outer surface 10 having a surface area S and having a living fruit outer surface portion 10a having a surface area

KS wherein $0.25 \leq K \leq 0.03$ (b) first analytical apparatus means 2118, 2124 and 2126 comprising first trapping tube means 2118 attached to first negative pressure pump means 2124 associated with first chemical analysis means 2126 (with the trapping tube means 2118 containing a trapping substance holding tube 2120 containing trapping substance (e.g., TENAX ®) 2122);

(c) a living flower 2102 (having stem 2106a/2106b attached to plant 2115 growing in ground 2114) located within a 3-dimensional space (shown to be hemispherical) 2130 (the hemispherical space 2130 is enclosed by shell 2101a having two insertion orifices therein 2142a and 2143), proximate and juxtaposed to said living fruit outer surface portion 10a, said living flower 2102 being connected to a living flower stem 2106a, which, in turn, is connected to a living flower plant 2115;

(d) the hollow flexible or rigid enclosure means 2101/2101a surrounding the living flower 2102, having an inner enclosure means void 2130 and an outer enclosure means shell 2101/2101a encompassing said void 2130, and terminating at an enclosure rim means 2103, said void (i) containing said living flower 2102 and (ii) being defined by said outer enclosure means shell 2101/2101a and said enclosure rim means 2103, said outer enclosure means shell 2101/2101a having first and second insertion orifices 2142a and 2143, respectively, each of which extends from said outer enclosure means surface to said inner enclosure means void 2130, said enclosure means (i) sealably gripping (using adhesive, for example, 36–36a) said first outer surface portion 10a of said living pineapple and (ii) surrounding said living flower 2102 whereby said living flower stem 2106a is fixedly held in place using packing 2144a in said first insertion orifice 2142a, said first trapping tube means 2118 being inserted through said second insertion orifice 2143 via tube 2123 causing it to be extended at 2147 into said enclosure means void 2130 whereby when said first negative pressure pump means 2124 is engaged, components of the aroma evolving (i) from said outer surface 10a of said living pineapple and (ii) from said living flower 2102 are entrapped in said first trapping tube means trapping substance 2122, simultaneously, enabling the contents of said first trapping tube means 2118 to be continuously analyzed substantially simultaneously using said first chemical analysis means indicated by reference numeral 2126. The continuation of stem 2106a is in 2106b. When the vacuum pump 2124 is engaged, during the engagement air (indicated by arrows 2140a) enters the enclosed 3-space 2130 and picks up aroma components from surface 10a and from flower 2102 and the aroma components are then forced through tube 2123 (indicated by the arrow) onto the TENAX ®, for example, 2122 in the first trapping tube means 2118.

In FIG. 1B, the surface 10a is broken (indicated using reference numeral 10b) exposing inner surface 11 to the 3-dimensional space 2130. Thus, the headspace 2130 includes aroma components from surface 11a (the inner surface of the living pineapple) as well as aroma components from living flower 2102.

Referring to FIG. 2, FIG. 2 shows apparatus 200 for quantitatively and qualitatively substantially continuously analyzing the aroma evolved:

(i) from a portion 10a of the outer surface 10 of a living pineapple (having inner volume 82) having stem 16, roots 14 and living in ground 12;
(ii) from within the pineapple; and
(iii) from a living flower 2102 located within a 3-dimensional space 2130 proximate and juxtaposed to said portion (unbroken) 10a of the outer surface 10 of said living pineapple.

A substantial portion of the outer surface 10 of the living pineappled is located at a given distance "h" (e.g., six inches) from the central axis 80 and an inner volume 82 surrounds the central axis 80 and is encompassed by the outer surface 10; and a depth core section 18 is removed from the inner volume 82 along a directional vector "V" extending substantially radially from the central axis 80 to the outer surface 10 within the inner volume 82. The depth core 18 has effective diameter, $D_1$ (e.g., about $\frac{1}{4}$″) equal to $2 \times$ (the effective radius, $R_1$ (about $\frac{1}{8}$″)) and a core section volume ranging from about $$\pi R_1^2 h$$

down to about $$\frac{\pi R_1^2 h}{2}$$

thereby forming a core section void within the living pineapple. Second analytical apparatus means in FIG. 2 comprises a second trapping tube means (22, 24) which is a glass outer tube 22 and a trapping tube 24 inserted through opening 20 into depth core 18. Attached to the trapping tribe 24 (which may, for example, contain TENAX ®GC) is tube 27 connected to a negative pressure pump means 26.

Reference numeral 86 represents analytical apparatus capable of providing GC-mass spectra of trapped substances which may be taken further together with spectral apparatus capable of providing infrared spectra of the trapped substances and apparatus capable of providing NMR spectra of the trapped substances.

In FIG. 2, first analytical apparatus means (for analyzing the aroma emitted from the surface portion 10a of the living pineapple of FIG. 2) comprises first trapping tube means 2118 inserted into enclosure 2101 which is sealably affixed using adhesive 36 (a sealing material is indicated by reference numeral 36 such as an epoxy resin) to a portion of the surface 10a of the living pineapple. The trapping tube means 2118 is connected to tube 2123 which is connected to negative pressure pump 2124 associated with analyzer 2126 (e.g., GC-mass spectral analyzer; nuclear magnetic resonance analyzer; and infrared analyzer). The apparatus is maintained in place in conjunction with the living pineapple of FIG. 2 which is held up by a living pineapple stem 16. The trapping tube is inserted into the enclosure means (e.g., a hemispherically shaped cup means having an inner cup means void 2130 and an outer cup means surface 2101a) surrounding the void 2130 and terminating at a substantially circular rim 2103 of radius $R_2$ with the inner volume of said cup means being about:

$$[\tfrac{2}{3}\pi R_2^3].$$

Thus, when the second negative pressure pump means 26 and the second negative pressure pump means 2124 are simultaneously engaged, components of the aroma evolving from the outer surface portion 10a of the living pineapple and from the living flower 2102 are entrapped in the first trapping tube means 2118 and the second trapping tube means 22 simultaneously, enabling the contents of the first trapping tube means and the second trapping tube means to be continuously analyzed substantially simultaneously using said first and second chemcial analysis means 2126 and 86, respectively.

Referring to FIGS. 4 and 5, there is provided a process for forming scented polymer pellets (wherein the polymer may be a thermoplastic polymer such as low density polyethylene or polypropylene or copolymers of ethylene-vinyl acetate or mixtures of a polymer and copolymer such as a copolymer of ethylene-vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower-most portion of the container is maintained at a slightly lower temperature and the material of the container is taken off at such location for delivery through the conduit. Thus, referring to FIGS. 4 and 5, in particular, the apparatus used in producing such elements comprises a device for forming the polymer containing perfume, e.g., polyethylene or polyethylene-polyvinyl acetate or mixtures of same or polypropylene, or the like, which comprises a vat or container 212 into which the polymer taken alone or in admixture with other copolymers and a perfuming substance containing at least one of the living flower/living fruit fragrances of our invention is placed. The container is closed by means of an air-tight lid 228 and clamped to the container by bolts 265. A stirrer 273 traverses the lid or cover 228 in an air-tight manner and is rotatable in a suitable manner.

A surrounding cylinder 212A having heated coils which are supplied with electric current through cable 214 from a rheostat or control 216 is operated to maintain the temperature inside the container 212 such that the polymer in the container will be maintained in the molten or liquid state. In has been found advantageous to employ polymers at such a temperature that the viscosity will be in the range of 90–100 sayboldt seconds.

Heating means (coils 212A) are operated to maintain the upper portion of the container 212 within a temperature range of, for example, 250°–260° C. in the case of low density polyethylene. The bottom portion of the container 212 is also heated by means of heating coils 212A regulated through the control 220 connected thereto through a connecting wire 222 to maintain the lower portion of the container 212 with a temperature range of 225°–240° C.

Thus, the polymer or mixture of polymers added to the container 212 is heated from 10–12 hours, whereafter the perfume composition or perfume material containing at least one of the living flower/living fruit fragrances of our invention is quickly added to the melt. Generally, about 10–45 percent by weight of the resulting mixture of the perfumery substance is added to the polymer.

After the perfume material containing at least one of the living flower/living fruit fragrances of our invention is added to the container 212, the mixture is stirred for a few minutes, for example, 5–15 minutes and maintained within the temperature ranges indicated previously by the heating coils 212A. The controls 216 and 220 are connected through cables 224 and 226 to a suitable supply of electric current for supplying the power for heating purposes.

Thereafter, the valve "V" is opened permitting the mass to flow outwardly through conduit 232 (also indicated by reference numeral 218 in FIG. 4) having a multiplicity of orifices 234 adjacent to the lower side thereof. The outer end of the conduit 232 is closed so that the liquid polymer intimately admixed with at least one of the living flower/living fruit fragrances of our invention will continuously drop through the orifices 234 downwardly from the conduit 232. During this time, the temperature of the polymer intimately admixed with the perfumery substance in the container 212 is accurately controlled so that a temperature in the range of from about 240°–250° C. (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance containing at least one of the living flower/living fruit fragrances of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into the container 245 which is advantageously filled with water or some other suitable cooling liquid to insure the rapid cooling of each of the pellets 244. The pellets 244 are then collected from the container 245 and utilized for formation of other functional products, e.g., garbage bags and the like. Belt 238 is optionally moistened from sponge 256 obtaining cooling liquid 254 held in container 250 having side walls 248.

The following examples are illustrative of processes for using the apparatus of our invention, processes for carrying out production of fragrance formulations of our invention and processes for using the living flower/living fruit fragrances of our invention. These examples are illustrative and the invention is to be considered to be restricted thereto only as indicated in the appended claims.

All parts and percentages given herein are by weight unless otherwise specified.

EXAMPLE I

Headspace Analysis and Fragrance Formulation Produced Therefrom Using Living Yellow Pineapple and Living Orange Rose [Cary Grant]

Apparatus was built as set forth in FIGS. 1 and 1A. The apparatus 100 consists of (i) a mature plant containing a ripe yellow color pineapple. To the outside of the pineapple was attached one-half of a 100 ml clam shaped headspace bifurcated flask with two inlet tubes, the flask being indicated by reference numeral 2101. The flask had a shell wall 0.125" in thickness; and an overall shell diameter of 8". Prior to putting the semi-hemispherical walls 2101a together, a living growing flower, orange rose (Cary Grant) 2102 was placed through opening 2142a. Thus, the orange rose (Cary Grant) flower 2102 was placed through opening 2142a and the two semi-hemispherical walls were then placed together around stem 2106a/2106b at orifices 2142a using stopper 2144a to hold the stem 2106a/2106b in place. Through orifice 2143 of shell 2101a is inserted tube 2123 connected to tube 2120 and outer tube 2118. In tube 2120 is TENAX®-GC, tube 2118 being a ⅛" diameter×4" long TENAX®-GC headspace trap. Tube 2120 is fabricated from glass being 5" in length×¼" outside diameter. The pump is a n-alpha-2-pump (vacuum pump), "a low flow" pump marketed by the Amatec Company of Largo, Fla. 34643 (the Amatec Company constant flow sampler). The shell 2101a is sealed using sealant 36 around the shell rim 2103 leaving surface 10a exposed.

The pump, indicated by reference numeral 2124 is then engaged and operated for a period of one hour. At the end of the one hour period, the pump is stopped and the TENAX® trap is removed. The TENAX® trap contains the following ingredients.

The headspace without the flower 2102 is also analyzed and the results of this analysis carried out using the same procedure as above is set forth below.

An individual sphere only containing orange rose (Cary Grant) flower, a living flower, is also tested in the same manner (without the yellow pineapple surface portion). The results of analysis of this headspace with orange rose (Cary Grant) living flower alone is also set forth below.

The results are set forth in the following Table I:

TABLE I

| Compound Identified | Area % For Orange Rose (Cary Grant) & Yellow Pineapple | Area % For Orange Rose (Cary Grant) Living Flower, Alone | Area % For Yellow Pineapple Surface Alone |
|---|---|---|---|
| Acetaldehyde | 0.93 | — | 0.90 |
| Acetic Acid | — | 0.09 | — |
| 2-Methyl Furan | 0.02 | 0.02 | — |
| 2-Ethyl-Furan | — | 0.01 | — |
| Methyl Acrylate | 0.13 | — | 1.73 |
| 2,3-Dihydro-4-Methyl Furan | — | 0.04 | — |
| Methyl Acetate | — | 0.01 | — |
| Methyl Propionate | 0.01 | — | 0.08 |
| Propanoic Acid | — | — | 0.03 |
| Ethyl Propanoate | — | — | 0.001 |
| n-Heptane | 0.001 | — | 0.15 |
| Messityl Oxide | — | 0.02 | — |
| Methyl Butyrate | 0.38 | — | 1.41 |
| Methyl Isovalerate | 0.01 | — | 0.01 |
| Methyl-2-Methyl Butyrate | 0.67 | — | 1.19 |
| n-Hexanal | 0.10 | — | 0.12 |
| Ethyl Butyrate | 0.13 | — | 0.05 |
| Butyl Acetate | 0.13 | — | — |
| n-Octane | 0.15 | 0.01 | 0.54 |
| Methyl Valerate | 0.38 | — | 0.58 |
| 2-Hexenal | 0.08 | 0.03 | — |
| Ethyl-2-Methyl Butyrate | 0.14 | — | 0.001 |
| 2,2,6-Trimethyl-3,4-Dihydro Pyran | — | 0.02 | — |
| Styrene | 0.08 | — | 0.001 |
| Cis-3-Hexenol | — | 0.001 | — |
| 1-Acetyl Cyclohexane | — | 0.04 | 0.001 |
| n-Heptanal | 0.29 | — | — |
| 3-Acetyl-3-Methyl Cyclopentene | — | 0.03 | — |
| Amyl Acetate | 0.84 | 0.12 | — |
| 2-Methyl-4,5-Dihydro Furan | — | 0.01 | — |
| Dimethyl Malonate | 0.001 | — | 0.001 |
| n-Nonane | 0.20 | — | 0.25 |
| Gamma-Valerolactone | — | 0.01 | — |

TABLE I-continued

| Compound Identified | Area % For Orange Rose (Cary Grant) & Yellow Pineapple | Area % For Orange Rose (Cary Grant) Living Flower, Alone | Area % For Yellow Pineapple Surface Alone |
|---|---|---|---|
| 3-Methyl-2-Buten-1-yl Acetate | 0.10 | 0.01 | — |
| Methyl Anisole | — | 0.02 | — |
| Methyl Hexanoate | 20.82 | — | 55.81 |
| Benzaldehyde | 1.96 | 0.80 | 0.31 |
| Benzonitrile | — | — | 0.001 |
| 6-Methyl-5-Hepten-2-One | 0.001 | 0.57 | — |
| Phenol | 0.36 | 0.10 | 0.20 |
| Benzyl Methyl Ether | 2.69 | 3.15 | — |
| Ethyl Hexanoate | 2.14 | — | 3.05 |
| Cis-3-Hexenyl Acetate | 5.43 | 16.18 | — |
| Hexyl Acetate | 1.60 | 6.01 | — |
| n-Decane | 0.27 | — | 0.25 |
| Methyl Heptanoate | 0.20 | — | 0.75 |
| d-Limonene | — | — | 0.001 |
| Benzyl Alcohol | 3.00 | 11.93 | — |
| Acetophenone | 0.20 | — | 0.38 |
| Trans,Trans-Hexa-2,4-Dienyl Acetate | — | 0.001 | — |
| Methyl Benzoate | 0.001 | 0.05 | — |
| Beta-Phenyl Ethyl Methyl Ether | — | 0.10 | — |
| Methyl Octanoate | 17.79 | — | 16.58 |
| n-Nonanal | — | 0.11 | 0.58 |
| Beta-Phenyl Ethyl Alcohol | 16.00 | 43.52 | — |
| Benzoic Acid | — | — | 0.001 |
| Benzyl Acetate | 1.86 | 2.23 | — |
| Beta-Phenyl Ethyl Formate | 0.05 | 0.001 | — |
| n-Decanal | — | 0.08 | 0.13 |
| n-Dodecane | — | 0.02 | — |
| Methyl Acetoacetate | 0.05 | — | 0.02 |
| 5-(Acetyloxy)-Pentenoic Acid, Methyl Ester | 0.48 | — | 3.38 |
| 5-(Acetyloxy)-Hexanoic Acid, Methyl Ester | 0.18 | — | 7.06 |
| Beta-Phenyl Ethyl Acetate | 18.19 | 13.57 | 0.29 |
| 3,5-Dimethoxy Toluene | 0.55 | — | 0.001 |
| Megastigma-7-(E),9,13-Triene | — | 0.01 | — |
| Theaspirane | 0.001 | 0.02 | — |
| Alpha-Cubebone | 0.10 | 0.01 | — |
| Methyl Decanoate | — | — | 0.09 |
| 5-(Acetyloxy)-Nonanoic Acid, Methyl Ester | 0.21 | — | 2.55 |
| Bourbonene | 0.15 | 0.02 | — |
| 2-Methyl-N-Phenyl-2-Propenamide | — | — | 0.11 |
| n-Tetradecane | 0.40 | 0.02 | — |
| Dihydro-Alpha-Ionone | 0.10 | 0.03 | — |
| n-Dodecanoic Acid | 0.10 | — | — |
| Geranyl Acetone | — | 0.06 | — |
| Beta-Ionone | 0.02 | 0.03 | — |
| Gamma Cadinene | — | 0.03 | — |
| Alpha-farnesene | — | 0.01 | — |
| n-Pentadecane | — | 0.15 | — |
| n-Heptadecane | 0.09 | 0.04 | — |
| Nonadecadiene-2,4 | 0.50 | 0.13 | —. |

The entrapped headspace analysis by GC/MS as set forth in the above Table I is set forth in FIGS. 3A, 3B and 3C; FIG. 3A for the combined orange rose (Cary Grant) flower and living pineapple surface section;

FIG. 3B for the orange rose (Cary Grant) living flower alone and FIG. 3C for the living yellow pineapple surface section alone.

The following perfume formulation was then prepared resulting from the analysis as set forth in FIG. 3A and as set forth in the first column of the above table; of the combined orange rose (Cary Grant) living flower and the living pineapple surface section analyses:

| Ingredients | Parts by Weight |
| --- | --- |
| Methyl hexanoate | 20.8 |
| Benzaldehyde | 2.0 |
| Benzyl methyl ether | 2.70 |
| Ethyl hexanoate | 2.10 |
| Cis-3-hexenyl acetate | 5.4 |
| n-Hexyl acetate | 1.6 |
| Benzyl alcohol | 3.0 |
| Methyl octanoate | 17.8 |
| Beta-Phenyl ethyl alcohol | 16.0 |
| Benzyl acetate | 1.9 |
| Beta-Phenyl ethyl acetate | 18.2 |

The resulting fragrance has an intense natural rose, fruity, dried fruit (apricot) aroma.

The contents of the traps in each of the experimental runs were analyzed by GC-MS analysis using a 50 m×0.032 OV-2 fused silica column having the conditions: (50°–220° C. temperature range at 3° C. per minute).

EXAMPLE II

Preparation of a Soap Composition

100 Grams of soap chips are admixed with 1 gram of the perfume substance prepared according to Example I until a substantially homogeneous composition is obtained. The perfumed soap manifests an excellent natural rose, fruity, dried fruit (apricot) aroma.

EXAMPLE III

Preparation of a Cologne and Handkerchief Perfume

The perfume substance prepared according to Example I is incorporated into a cologne at concentrations of 1.5%, 2.0%, 2.5%, 3.0%, 3.5% and 4.0% in 80%, 85%, 90% and 95% aqueous ethanol and into handkerchief perfumes at concentrations of 15%, 20%, 25% and 30% (in 85%, 90% and 95% aqueous ethanol). A distinct and definitive intense and long-lasting natural rose, fruity, dried fruit (apricot) aroma is imparted to the cologne and to the handkerchief perfume at each of the levels indicated.

EXAMPLE IV

Utilizing the procedure of Example I of Column 15 of U.S. Pat. No. 3,632,396 the specification for which is incorporated by reference herein, a non-woven cloth substrate useful as a drier-added fabric-softening article of manufacture is prepared wherein the substrate, the substrate coating and the outer coating and the perfuming material are as follows:

1. a water "dissolvable" paper ("Dissolvo paper");
2. Adogen 448 (melting point about 140° F.) as the substrate coating; and
3. an outer coating having the following formulation (melting point about 150° F.):
   57 percent—$C_{20-22}$HAPS (3-(N-alkyl-N,N-dimethyl ammonio)-2-hydroxy propane-1-sulfonate wherein the alkyl is a mixture of alkyls having from 20 to 22 carbon atoms)
   27 percent—isopropyl alcohol
   20 percent—antistatic agent
   1 percent—of the perfume substance prepared according to Example I.

Fabric-softening compositions prepared as set forth above having an intense and long-lasting rosey, fruity, dried fruit (apricot) aroma essentially consists of a substrate having a weight of about 1.85 grams per 100 square inches of substrate and a summed outer coating of about 1.4 grams per 100 square inches of substrate thereby providing a total aromatized substrate and an outer coating weight ratio of about 1:1 by weight of the substrate. A fruity, rose, dried fruit (apricot) aroma is imparted to the headspace in the dryer on operation thereof using the said dryer added fabric softening non-woven fabric.

EXAMPLE V

Preparation of a Soap Composition

100 Grams of soap chips are prepared according to Example V of U.S. Pat. No. 4,058,490 issued on Nov. 15, 1977 the specification for which is incorporated herein by reference, as follows:

"The sodium salt of an equal mixture of $C_{10}$–$C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water 0.2 lb. titanium hydroxide."

The resulting blend is then mixed with the perfume substance of Example I until a substantially homogeneous composition is obtained. The perfumed soap composition manifests an excellent intense and long-lashing natural rose, fruity, dried fruit (apricot) aroma.

EXAMPLE VI

Granular Detergent Composition

A granular detergent composition is prepared according to United Kingdom Patent No. 1,501,498 the specification for which is incorporated by reference herein having the following formula. It is prepared by spray-drying the following mixture:

| Ingredient | Parts by Weight |
| --- | --- |
| Sodium salt of ethoxylated fatty alcohol sulfate having an average of about 2.25 moles of ethylene oxide per mole of fatty alcohol | 14.1 |
| Sodium tallow alkyl sulfate | 2.4 |
| Sodium silicate solids ratio | 6.0 |
| $SiO_2/Na_2O$ = 2.0 | 6.0 |
| Sodium tripolyphosphate | 24.0 |
| $Na_{12}(AlO_2SiO_2)_{27}H_2O$ | 18.0 |
| Moisture | 10.0 |
| Sodium sulfate | 25.0 |
| Perfume substance of Example 1 | 4.0 |

Laundry solutions containing the above detergent compositions are used to launder fabrics. Each of the laundry compositions both prior to and on laundering give rise to a pleasant long-lasting aroma which can be described as "a natural rose aroma with fruity and dried fruit (apricot) nuances.

EXAMPLE VII

Perfumed Liquid Detergent

Concentrated liquid detergents are prepared with rose, fruity, dried fruit (apricot) aromas containing 0.10%, 0.15% and 0.20% of the perfume compositions of Example I in the liquid detergent. The liquid detergent is a builder free liquid detergent consisting of (a) 50% of a nonionic surfactant having a HBL of 8.0 and a critical micelle concentration of 0.007 weight percent at 25° C.; (b) an anionic surfactant which is a triethanolamine prepared according to United Kingdom Patent No. 1,491,603 the specification for which is incorporated by reference herein.

The detergents all possess a natural rose aroma with fruity, dried fruit (apricot) nuances.

EXAMPLE VIII

Preparation of a Detergent Composition

A total of 100 grams of detergent powder (a low phosphate content detergent composition which contains 12% by weight phosphate builder, 8 percent hardness mineral ion insensitive detergent, 0.9 percent by weight maleic anhydride-vinyl chloride copolymer and 2 percent alkylene oxide condensation product prepared according to Example IV at column IX, U.S. Pat. No. 4,000,080 issued on Dec. 28, 1976, (the specification for which is incorporated by reference herein) is intimately admixed with 0.15 grams of the perfume composition of Example I until a substantially homogeneous composition is obtained. The composition has an intense and long-lasting rose, fruity, dried fruit (apricot) aroma.

EXAMPLE IX

The fragrance composition of Example I is added to a 50:50 weight:weight mixture of low density polyethylene:polyepsilon caprolactone PCL-700 forming pellets with a rose, fruity, dried fruit (apricot) aroma.

75 Pounds of a mixture of PCL-700 polyepsilon caprolactone (manufactured by the Union Carbide Corporation of New York, N.Y. having a melting point of about 180°-190° F.): low density polyethylene are heated to about 250° C., in a container of the kind illustrated in FIGS. 4 and 5. 25 Pounds of the fragrance material prepared according to Example I is then quickly added to the liquified polymer mixture. The lid 228 is put in place and the agitating means 273 are actuated. The temperature is then raised to about 260° F. and the mixing is continued for 5-15 minutes. The valve "V" is then opened to allow flow of the molten polymer enriched with the perfume composition of Example I to exit through the orifices 234. The liquid falling through the orifices 234 solidified almost instantaneously upon impact with the moving cooled conveyor 238. Polymer beads or pellets 244 having a rose, fruity, dried fruit (apricot) aroma are thus formed. Analysis demonstrates that the pellets contain about 25% of the fragrance composition of Example I so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have an intense and long-lasting natural rose, fruity, dried fruit (apricot) aroma.

The sheets of films are cut into strips of 0.25" in width × 3" in length and placed into room air fresheners.

On operation of the room air freshener, after four minutes, the room in each case has an aesthetically pleasing aroma with no foul odor being present, the aroma being described as "natural rose, fruity, dried fruit (apricot)".

EXAMPLE X

The LIVING FLOWER ®/LIVING FRUIT ® perfume composition of Example I is admixed with CLARYCET ™ (trademark of International Flavors & Fragrances Inc. for the ester having the structure:

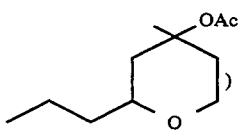

in the ratio of 10 parts by weight of ester to one part by weight of LIVING FLOWER ®/LIVING FRUIT ® perfume composition. At the rates of:

100 ppm;
150 ppm; and
200 ppm the resulting composition is added to EXXON ® middle distillate fuel heating oil in accordance with the procedure of European Published Application 532,556 published on Mar. 24, 1990 (corresponding to PCT Application 91/18961-A).

On use, in each case, the unpleasant "burnt fuel oil" nuances are completely masked and a "faint pleasant aroma" which can be described as natural rose, fruity, dried fruit (apricot) is imparted to the environment surrounding the burning heating oil.

What is claimed is:

1. A process for quantitatively and qualitatively substantially continuously analyzing the aroma emitted and rate of emission of the aroma components thereof:
   (i) from a portion of the outer surface of a living fruit; and
   (ii) from a living flower located within an enclosed 3-dimensional space proximate and juxtaposed with said portion of the outer surface of said living fruit consisting essentially of the steps of:

(a) providing a living fruit having a living fruit outer skin surface and a living fruit inner surface; said outer surface having a surface area S, and having a living fruit outer surface portion having a surface area

KS wherein 0.25 ≦ K ≦ 0.03

(b) providing analytical apparatus means comprising a trapping tube means attached to negative pressure pump means associated with chemical analysis means;

(c) providing a living flower located within an enclosed 3-dimensional space proximate and juxtaposed with said living fruit outer surface portion, said living flower connected to a living flower stem, which, in turn, is connected to a living flower plant or living flower tree;

(d) providing hollow flexible or rigid enclosure means surrounding said living flower having an inner enclosure means void and an outer enclosure means shell having an outer enclosure means surface and an inner enclosure means surface, said outer enclosure means shell encompassing said void and terminating at an enclosure rim means, said void (i) containing said living flower and (ii) being defined by said outer enclosure means shell and said enclosure rim means, said outer enclosure means shell having first and second insertion orifices, each extending from said outer enclosure means surface to said inner enclosure means void, said enclosure means being capable of sealably gripping said outer surface portion of living fruit;

(e) causing said enclosure means to (i) sealably grip said outer surface portion of said living fruit at said enclosure rim means and (ii) surround said living flower whereby said living flower stem is fixedly held in place using said first insertion orifice;

(f) inserting said trapping tube means through said second insertion orifice causing it to be extended into said enclosure means void;

(g) engaging said negative pressure pump means whereby components of (i) the aroma evolving from said outer surface portion of said living fruit and (ii) the aroma evolving from said living flower, are simultaneously entrapped in said first trapping tube means; and (h) analyzing the contents of said first trapping tube means using said first chemical analysis means substantially continuously.

2. A process for quantitatively and qualitatively substantially continuously analyzing the aroma emitted and rate of emission of the aroma components thereof:

(i) from within a living fruit;
(ii) from a portion of the outer surface of a living fruit; and
(iii) from a living flower located proximate to and juxtaposed to said outer surface portion of said living fruit simultaneously consisting essentially of the steps of:

(a) providing a living fruit having a living fruit outer skin surface and a living fruit inner surface, said outer surface having a surface area S and having a living fruit outer surface portion having a surface area $$KS$$

wherein $$0.25 \leq K \leq 0.03$$

said living fruit being located on a given central axis, said outer surface portion of said living fruit being located at a given distance, "h" from said central axis and an inner volume surrounding said central axis and encompassed by said outer surface;

(b) removing a depth core section from said inner volume of said living fruit running from said outer surface of said living fruit to a depth of from about $$\text{``}\tfrac{1}{2}h\text{''}$$

up to "h" into said inner volume along a directional vector "v" extending substantially radially from said central axis of said living fruit to said outer surface of said living fruit within said inner volume, said depth core section having an effective diameter, $D_1$ equal to $2 \times$ (effective radius, $R_1$) and a core section volume ranging from about $$\frac{\pi R_1^2 h}{2}$$

up to about $$\pi R_1^2 h$$

thereby forming a core section void within said living fruit; then (c)-1 providing first analytical apparatus means comprising first trapping tube means attached to first negative pressure pump means associated with first chemical analysis means;

(c)-2 providing second analytical apparatus means comprising a second trapping tube means attached to second negative pressure pump means associated with second chemical analysis means;

(d) providing a living flower located within an enclosed 3-dimensional space proximate and juxtaposed with said living fruit outer surface portion, said living, flower being connected to a living flower stem, which, in turn, is connected to a living flower plant or living flower tree;

(e) providing hollow flexible or rigid enclosure means surrounding said living flower having an inner enclosure means void and an outer enclosure means shell having an outer enclosure means surface and an inner enclosure means surface, said outer enclosure means shell encompassing said void and terminating at an enclosure rim means, said void (i) containing said living flower and (ii) being defined by said outer enclosure means shell and said enclosure rim means, said outer enclosure means shell having first and second insertion orifices, each extending from said outer enclosure means surface to said inner enclosure means void, said enclosure means being capable of sealably gripping said outer surface portion of said living fruit at said enclosure rim means;

(f) causing said enclosure means to (i) sealably grip said outer surface portion of said living fruit at said enclosure rim means and (ii) surround said living flower whereby said living flower stem is fixedly held in place using said first insertion orifice;

(g) inserting said first trapping tube means through said second insertion orifice, causing it to be extended into said enclosure means void;

(h) inserting said second trapping tube means into said core section void of said living fruit along said directional vector "v";

(j) simultaneously engaging said first negative pressure pump means and said second negative pressure pump means, whereby components of the aroma evolving from said outer surface portion of said living fruit and components of the aroma evolving from said living flower are entrapped in said first trapping tube means and components of the aroma evolving from within said living fruit are entrapped in said second trapping tube means, simultaneously; and (k) analyzing the contents of said first trapping tube means using said first chemical analysis means and said second trapping tube means using said second chemical analysis means substantially continuously and substantially simultaneously.

3. Apparatus for quantitatively and qualitatively substantially continuously analyzing the aroma evolved:

(i) from a portion of the outer surface of a living fruit; and (ii) from a living flower located within a 3-dimensional space proximate and juxtaposed to said portion of the outer surface of said living fruit, consisting essentially of:

(a) a living fruit having a living fruit outer skin surface and a living fruit inner surface, said outer surface having a surface area S and having a living fruit outer surface portion having a surface area $$KS$$

wherein $$0.25 \leq K \leq 0.03;$$

(b) analytical apparatus means comprising first trapping tube means attached to negative pressure pump means associated with chemical analysis means;

(c) a living flower located within a 3-dimensional space proximate and juxtaposed to said living fruit outer surface portion, said living flower connected to a living flower stem, which, in turn, is connected to a living flower plant or living flower tree;

(d) hollow, flexible or rigid enclosure means surrounding said living flower having an inner enclosure means void and an outer enclosure means shell, said outer enclosure means shell encompassing said void and terminating at an enclosure rim means, said void (i) containing said living flower and (ii) being defined by said outer enclosure means shell and said enclosure rim means, said outer enclosure means shell having first and second insertion orifices each of which extends from said outer enclosure means surface to said inner enclosure means void, said enclosure means (i) sealably gripping said outer surface portion of said living fruit and (ii) surrounding said living flower whereby said living flower stem is fixedly held in place using said insertion orifice, said first trapping tube means being inserted through said second insertion orifice causing it to be extended into said enclosure means void whereby, when said negative pressure pump means is engaged, components of the aroma evolving (i) from said outer surface portion of said living fruit and (ii) said living flower are entrapped in said trapping tube means simultaneously, enabling the contents of said first trapping tube means to be continuously analyzed substantially simultaneously using said chemical analysis means.

4. Apparatus for quantitatively and qualitatively substantially continuously analyzing the aroma evolved:

(i) from within a living fruit;

(ii) from an outer surface portion of said living fruit; and (iii) from a living flower located proximate to and juxtaposed to said outer surface portion of said living fruit consisting essentially of:

(a) a living fruit having a living fruit outer skin surface and a living fruit inner surface, said outer surface having a surface area S and having a living fruit outer surface portion having a surface area:

$$KS$$

wherein $$0.25 \leq K \leq 0.03$$

said living fruit being located on a given central axis, said outer surface of said living fruit being located at a given distance "h" from said central axis; an inner volume surrounding said central axis and encompassed by said outer surface; a depth core section being removed from said inner volume running from said outer surface to a depth of from about $$\text{``}\tfrac{1}{2}h\text{''}$$

up to "h" into said inner volume along a directional vector "v" extending substantially radially from said central axis to said outer surface within said inner volume, said depth core section having an effective diameter $D_1$ equal to $2 \times$(effective radius, $R_1$) and a core section volume ranging from about $$\pi R_1^2 h$$

up to about $$\frac{\pi R_1^2 h}{2}$$

thereby forming a core section void within said living fruit;

(b)-1 first analytical apparatus means comprising first trapping tube means attached to first negative pressure pump means associated with first chemical analysis means;

(b)-2 second analytical apparatus means comprising second trapping tube means attached to second negative pressure pump means associated with second chemical analysis means;

(c) a living flower located within a 3-dimensional space proximate to and juxtaposed with said living fruit outer surface portion, said living flower connected to a living flower stem, which, in turn, is connected to a living flower plant or living flower tree;

(d) hollow flexible enclosure means surrounding said living flower having an inner enclosure means void and an outer enclosure means shell, said outer enclosure means shell encompassing said void and terminating at an enclosure rim means, said void (i) containing said living flower and (ii) being defined by said outer surface means shell and said enclosure rim means, said outer enclosure means shell having first and second insertion orifices each of which extends from said outer enclosure means surface to said inner enclosure means void, said enclosure means (i) sealably gripping said outer surface portion of said living fruit and (ii) surrounding said living flower whereby said living flower stem is fixedly held in place using said first insertion orifice, said first trapping tube means being inserted through said second insertion orifice causing it to be extended into said enclosure means void;

(e) said second trapping tube means being inserted into said core section void of said living fruit along said directional vector "v";

whereby, when said first negative pressure pump means and said second negative pressure pump means are simultaneously engaged, components of the aroma evolving from (i) said outer surface portion of said living fruit and said living flower are entrapped in said first trapping tube means and components of the aroma evolving from within said living fruit are entrapped in said second trapping tube means, simultaneously, enabling the contents of said first trapping tube means and said second trapping tube means to be continuously analyzed substantially simultaneously using said first and second chemical analysis means.

5. The apparatus of claim 3 wherein the hollow flexible or rigid enclosure means is a hemispherically-shaped cup means having an inner cup means void and an outer cup means surface surrounding said void and terminating at a substantially circular rim of radius $R_2$ with the inner volume of said cup means being about $$[\tfrac{2}{3}\pi R_2^3].$$

6. The apparatus of claim 4 wherein the hollow flexible or rigid enclosure means is a hemispherically-shaped cup means having an inner cup means void and an outer cup means surface surrounding said void and terminating at a substantially circular rim of radius $R_2$ with the inner volume of said cup means being about $$[\tfrac{2}{3}\pi R_2^3].$$

7. The process of claim 1 wherein the living fruit is a living pineapple.

8. The process of claim 2 wherein the living fruit is a living pineapple.

9. The process of claim 1 wherein the living flower is a living rose.

10. The process of claim 2 wherein the living flower is a living rose.

11. The process of claim 7 wherein the living flower is a living rose.

12. The process of claim 8 wherein the living flower is a living rose.

13. A process for preparing a perfume composition comprising the steps of:
(i) providing from at least one independent source at least the major aroma components determined by the analysis of step (h) of claim 1; and
(ii) admixing the components provided by step (i) above.

14. A process for preparing a perfume composition comprising the steps of:
(i) providing from at least one independent source at least the major aroma components determined by the analysis of step (k) of claim 2; and
(ii) admixing the components provided by step (i) above.

15. A process for preparing a perfume composition comprising the steps of:
(i) providing from at least one independent source at least the major aroma components determined by the analysis of step (h) of claim 7; and
(ii) admixing the components provided by step (i) above.

16. A process for preparing a perfume composition comprising the steps of:
(i) providing from at least one independent source at least the major aroma components determined by the analysis of step (k) of claim 8; and
(ii) admixing the components provided by step (i) above.

17. A process for preparing a perfume composition comprising the steps of:
(i) providing from at least one independent source at least the major aroma components determined by the analysis of step (h) of claim 9; and
(ii) admixing the components provided by step (i) above.

18. A process for preparing a perfume composition comprising the steps of:
(i) providing from at least one independent source at least the major aroma components determined by the analysis of step (k) of claim 10; and
(ii) admixing the components provided by step (i) above.

19. A process for preparing a perfume composition comprising the steps of:
(i) providing from at least one independent source at least the major aroma components determined by the analysis of step (h) of claim 11; and
(ii) admixing the components provided by step (i) above.

20. A process for preparing a perfume composition comprising the steps of:
(i) providing from at least one independent source at least the major aroma components determined by the analysis of step (k) of claim 12; and
(ii) admixing the components provided by step (i) above.

21. A process for preparing a perfumed polymer comprising the step of intimately admixing in the liquid phase or in a solid phase a thermoplastic polymer with an aroma imparting quantity of a perfume composition formulated according to the process of claim 13.

22. A process for producing a perfumed article comprising the step of intimately admixing a perfumed article base with an aroma augmenting, enhancing or imparting quantity of a perfume composition formulated according to the process of claim 13.

23. A process for preparing a cologne comprising the step of intimately admixing water, ethanol and an aroma imparting quantity of a perfume composition formulated according to the process of claim 13.

* * * * *